(12) United States Patent
Rieckmann et al.

(10) Patent No.: US 10,737,085 B2
(45) Date of Patent: Aug. 11, 2020

(54) MEDICAL DEVICE WITH HEMOSTATIC VALVE

(71) Applicant: Greatbatch Ltd., Clarence, NY (US)

(72) Inventors: Hans P. Rieckmann, Minneapolis, MN (US); Hans Pflaumer, Apex, NC (US); Grant A. Scheibe, Loretto, MN (US); Biswa P. Das, Tonawanda, NY (US); Joseph E. Lesser, St. Louis Park, MN (US); Thomas E. Bailey, Brooklyn Park, MN (US)

(73) Assignee: Greatbatch Ltd., Clarence, NY (US)

( * ) Notice: Subject to any disclaimer, the term of this patent is extended or adjusted under 35 U.S.C. 154(b) by 158 days.

(21) Appl. No.: 15/970,927

(22) Filed: May 4, 2018

(65) Prior Publication Data
US 2018/0318571 A1 Nov. 8, 2018

Related U.S. Application Data

(60) Provisional application No. 62/501,876, filed on May 5, 2017, provisional application No. 62/501,801, filed on May 5, 2017.

(51) Int. Cl.
*A61M 39/06* (2006.01)
*A61M 25/00* (2006.01)
(Continued)

(52) U.S. Cl.
CPC .... *A61M 39/0606* (2013.01); *A61M 25/0097* (2013.01); *A61M 39/02* (2013.01);
(Continued)

(58) Field of Classification Search
CPC .......... A61M 39/06; A61M 2039/0633; A61M 2039/064; A61M 2039/062;
(Continued)

(56) References Cited

U.S. PATENT DOCUMENTS 4,000,739 A * 1/1977 Stevens ................. A61M 25/00
604/537
4,610,665 A * 9/1986 Matsumoto ....... A61M 39/0606
604/167.04

(Continued)

FOREIGN PATENT DOCUMENTS

EP         2533848 B1    5/2017
WO       1998013083       4/1998
(Continued)

OTHER PUBLICATIONS

European Search Report, Application No. 18170912.2, dated Jun. 8, 2018.

*Primary Examiner* — Laura A Bouchelle
(74) *Attorney, Agent, or Firm* — Michael P. Horvath

(57) ABSTRACT

In various examples, a hub for a medical device includes a hub housing including a passage from a proximal end of the hub housing to a distal end of the hub housing. A valve is disposed within the hub. The valve is configured to allow passage of an insertable device through the valve while inhibiting leakage of fluid from the valve. A cap is engaged to the hub housing. The cap includes an opening therethrough sized and shaped to allow passage of the insertable device through the opening. The opening allows access to the passage of the hub housing. An angled sidewall is disposed within the hub. The angled sidewall is configured to retain and deform the valve into a curved shape.

20 Claims, 15 Drawing Sheets

(51) Int. Cl.
*A61M 39/02* (2006.01)
*A61M 25/06* (2006.01)

(52) U.S. Cl.
CPC ........ *A61M 39/06* (2013.01); *A61M 39/0693* (2013.01); *A61M 25/0662* (2013.01); *A61M 2025/0098* (2013.01); *A61M 2039/0205* (2013.01); *A61M 2039/0235* (2013.01); *A61M 2039/062* (2013.01); *A61M 2039/064* (2013.01); *A61M 2039/068* (2013.01); *A61M 2039/0626* (2013.01)

(58) Field of Classification Search
CPC .. A61M 2039/0626; A61M 2039/0653; A61M 2039/066
See application file for complete search history.

(56) References Cited

U.S. PATENT DOCUMENTS

| | | | |
|---|---|---|---|
| 4,610,674 A | 9/1986 | Suzuki et al. | |
| 4,626,245 A | 12/1986 | Weinstein | |
| 4,629,450 A | 12/1986 | Suzuki et al. | |
| 4,673,393 A | 6/1987 | Suzuki et al. | |
| 4,798,594 A | 1/1989 | Hillstead | |
| 4,874,378 A | 10/1989 | Hillstead | |
| 4,895,565 A | 1/1990 | Hillstead | |
| 4,909,798 A | 3/1990 | Fleischhacker et al. | |
| 5,006,113 A | 4/1991 | Fischer | |
| 5,041,095 A | 8/1991 | Littrell | |
| 5,066,285 A | 11/1991 | Hillstead | |
| 5,071,411 A | 12/1991 | Hillstead | |
| 5,092,857 A | 3/1992 | Fleischhacker | |
| 5,104,389 A | 4/1992 | Deem et al. | |
| 5,106,363 A | 4/1992 | Nobuyoshi | |
| 5,125,903 A | 6/1992 | McLaughlin et al. | |
| 5,167,637 A | 12/1992 | Okada et al. | |
| 5,176,652 A | 1/1993 | Littrell | |
| 5,207,656 A | 5/1993 | Kranys | |
| 5,242,413 A | 9/1993 | Heiliger | |
| 5,324,271 A | 6/1994 | Abiuso et al. | |
| 5,350,363 A * | 9/1994 | Goode .............. | A61M 39/0606 604/167.04 |
| 5,409,464 A | 4/1995 | Villalobos | |
| 5,423,762 A | 6/1995 | Hillstead | |
| 5,453,095 A | 9/1995 | Davila et al. | |
| 5,460,616 A | 10/1995 | Weinstein et al. | |
| 5,520,655 A | 5/1996 | Davila et al. | |
| 5,538,505 A | 7/1996 | Weinstein et al. | |
| 5,562,632 A | 10/1996 | Davila et al. | |
| 5,591,137 A | 1/1997 | Stevens | |
| 5,643,227 A | 7/1997 | Stevens | |
| 5,720,734 A | 2/1998 | Copenhaver et al. | |
| 5,807,350 A | 9/1998 | Diaz | |
| 5,843,044 A | 12/1998 | Moorehead | |
| 5,897,497 A | 4/1999 | Fernandez | |
| 5,911,710 A | 6/1999 | Barry et al. | |
| 5,944,697 A | 8/1999 | Biche | |
| 6,142,981 A | 11/2000 | Heck et al. | |
| 6,149,632 A * | 11/2000 | Landuyt .................. | A61M 5/00 604/201 |
| 6,322,541 B2 * | 11/2001 | West ................. | A61M 39/0606 137/844 |
| 6,338,725 B1 | 1/2002 | Hermann et al. | |
| 6,358,230 B1 | 3/2002 | Davey | |
| 6,416,499 B2 | 7/2002 | Paul | |
| 6,551,283 B1 | 4/2003 | Guo et al. | |
| 6,569,120 B1 | 5/2003 | Green et al. | |
| 6,663,599 B2 | 12/2003 | Osborne et al. | |
| 6,776,774 B2 | 8/2004 | Tansey et al. | |
| 6,854,484 B2 | 2/2005 | Geyer et al. | |
| 7,081,106 B1 | 7/2006 | Guo et al. | |
| 7,166,088 B2 | 1/2007 | Heuser | |
| 7,182,753 B2 | 2/2007 | Matsumoto | |
| 7,637,893 B2 | 12/2009 | Christensen et al. | |
| 7,699,193 B2 | 4/2010 | Feierabend | |
| 7,766,898 B2 | 8/2010 | Mottola et al. | |
| 7,931,253 B1 | 4/2011 | Paczonay | |
| 7,951,121 B2 | 5/2011 | Weaver et al. | |
| 7,985,232 B2 | 7/2011 | Potter et al. | |
| 8,016,791 B2 | 9/2011 | Sugiki et al. | |
| 8,047,229 B2 | 11/2011 | Adams et al. | |
| 8,048,039 B2 | 11/2011 | Carlyon et al. | |
| 8,096,976 B2 | 1/2012 | Sugiki et al. | |
| 8,105,314 B2 | 1/2012 | Fangrow | |
| 8,137,321 B2 | 3/2012 | Argentine | |
| 8,206,359 B1 | 6/2012 | Fischell | |
| 8,308,692 B2 | 11/2012 | McQueen et al. | |
| 8,377,011 B2 | 2/2013 | Weaver et al. | |
| 8,506,533 B2 | 8/2013 | Carlyon et al. | |
| 8,568,130 B2 | 10/2013 | Ouviev | |
| 8,628,056 B2 | 1/2014 | Labean et al. | |
| 8,662,104 B2 | 3/2014 | Hansmann et al. | |
| 8,679,074 B2 | 3/2014 | Daly et al. | |
| 8,721,461 B2 | 5/2014 | Lamothe et al. | |
| 8,753,317 B2 | 6/2014 | Osborne et al. | |
| 8,864,649 B2 | 10/2014 | Cahill et al. | |
| 9,126,018 B1 | 9/2015 | Garrison | |
| 9,144,462 B2 | 9/2015 | Lampropoulos et al. | |
| 9,174,036 B2 | 11/2015 | Okamura et al. | |
| 9,265,917 B2 | 2/2016 | Okamura et al. | |
| 9,320,831 B2 | 4/2016 | Trapp | |
| 9,533,137 B2 | 1/2017 | Fangrow | |
| 9,549,835 B2 | 1/2017 | Schreck et al. | |
| 9,586,028 B2 | 3/2017 | Okamura et al. | |
| 9,642,984 B2 | 5/2017 | Schumacher et al. | |
| 9,737,699 B2 | 8/2017 | Saab | |
| 2003/0014015 A1 | 1/2003 | Tansey et al. | |
| 2006/0084927 A1 | 4/2006 | Formichi | |
| 2006/0142699 A1 | 6/2006 | Lampropoulos | |
| 2006/0161102 A1 | 7/2006 | Newcomb et al. | |
| 2009/0012476 A1 | 1/2009 | Catlin | |
| 2009/0209914 A1 | 8/2009 | Koch et al. | |
| 2010/0076384 A1 | 3/2010 | Trask et al. | |
| 2010/0268163 A1 | 10/2010 | Rowe et al. | |
| 2010/0280463 A1 | 11/2010 | Murayama et al. | |
| 2011/0005629 A1 | 1/2011 | Ostrander et al. | |
| 2011/0021994 A1 | 1/2011 | Anderson et al. | |
| 2011/0166455 A1 | 7/2011 | Cully et al. | |
| 2012/0109060 A1 | 5/2012 | Kick et al. | |
| 2012/0172840 A1 | 7/2012 | Guo et al. | |
| 2012/0221024 A1 | 8/2012 | Sutton et al. | |
| 2012/0245527 A1 | 9/2012 | Stephens et al. | |
| 2013/0046241 A1 | 2/2013 | Okamura et al. | |
| 2013/0150792 A1 | 6/2013 | Alonso et al. | |
| 2013/0237923 A1 | 9/2013 | Ueda et al. | |
| 2013/0289531 A1 | 10/2013 | Pagan et al. | |
| 2014/0025044 A1 | 1/2014 | Zamarripa et al. | |
| 2014/0025103 A1 | 1/2014 | Hundertmark et al. | |
| 2014/0039263 A1 | 2/2014 | Le | |
| 2014/0114286 A1 | 4/2014 | Okamura | |
| 2014/0180066 A1 | 6/2014 | Stigall | |
| 2014/0187964 A1 * | 7/2014 | Corl ..................... | B06B 1/0622 600/467 |
| 2014/0207069 A1 | 7/2014 | Bierman et al. | |
| 2014/0343512 A1 | 11/2014 | Fischer et al. | |
| 2015/0032056 A1 | 1/2015 | Okamura et al. | |
| 2015/0133865 A1 | 5/2015 | Okamura et al. | |
| 2015/0327843 A1 | 11/2015 | Garrison | |
| 2016/0331930 A1 | 11/2016 | Okamura | |
| 2016/0361517 A1 | 12/2016 | Yazaki | |
| 2017/0232236 A1 | 8/2017 | Al-Rashdan et al. | |

FOREIGN PATENT DOCUMENTS

| | | |
|---|---|---|
| WO | 9906099 | 2/1999 |
| WO | 2016036468 | 3/2016 |

* cited by examiner

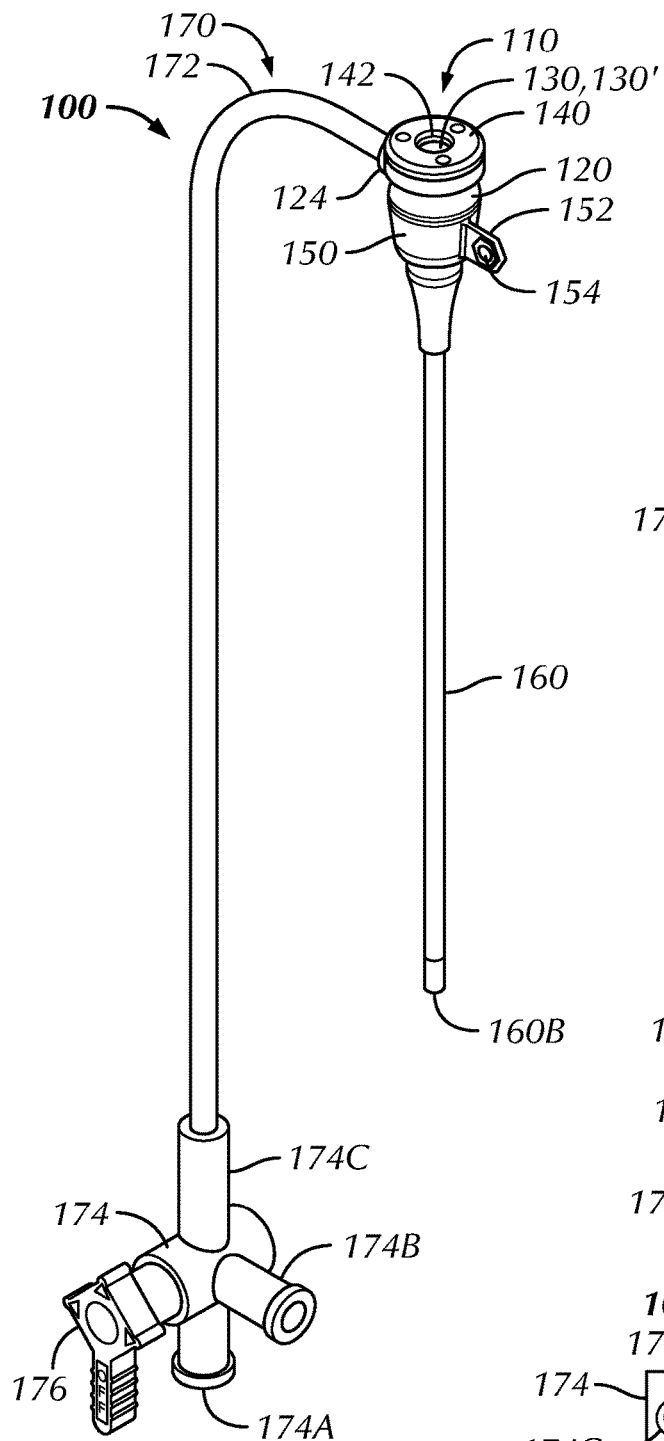
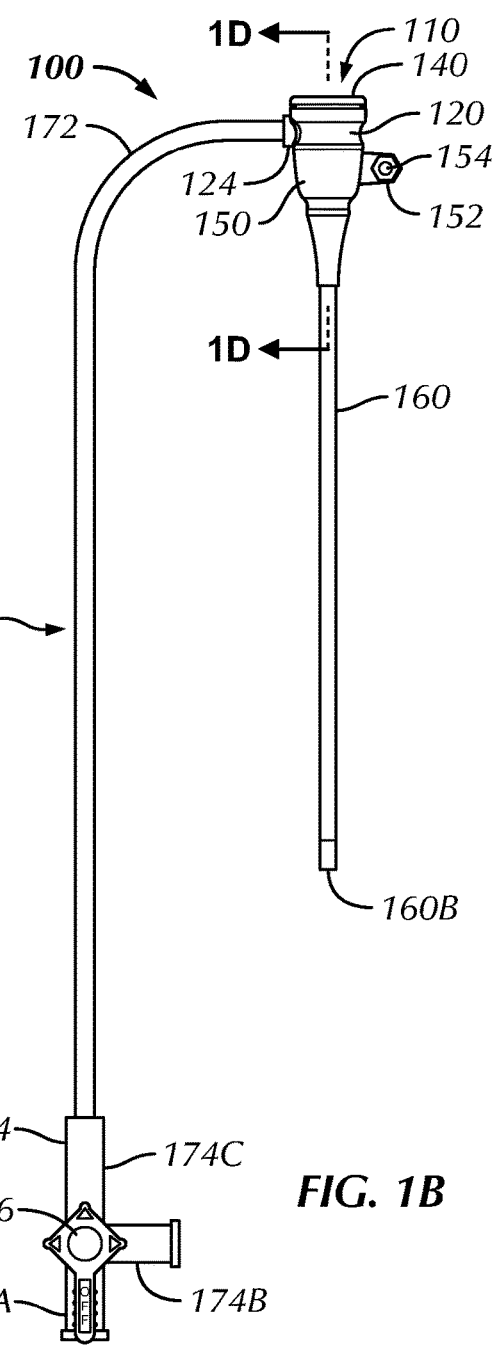
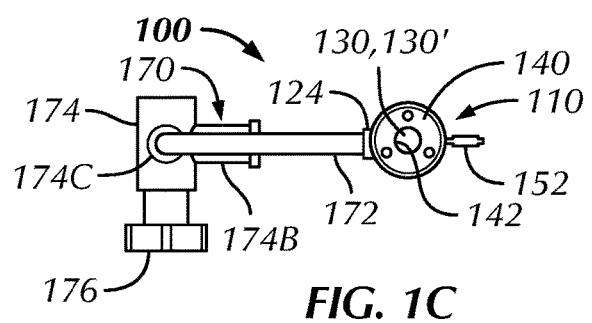
FIG. 1A
FIG. 1B
FIG. 1C

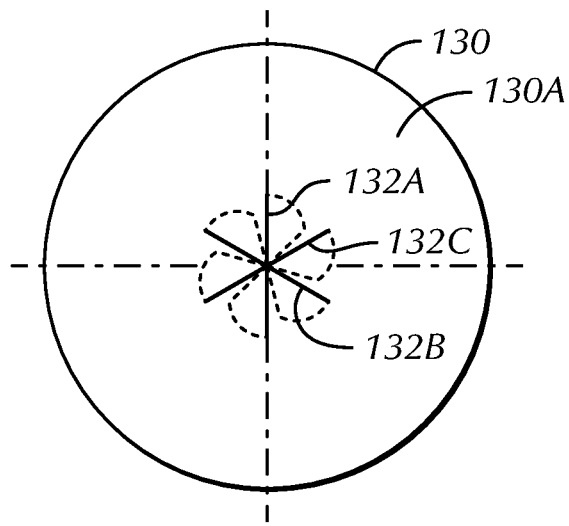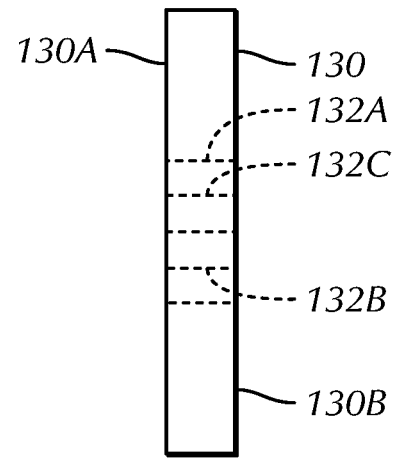
FIG. 3A    FIG. 3B
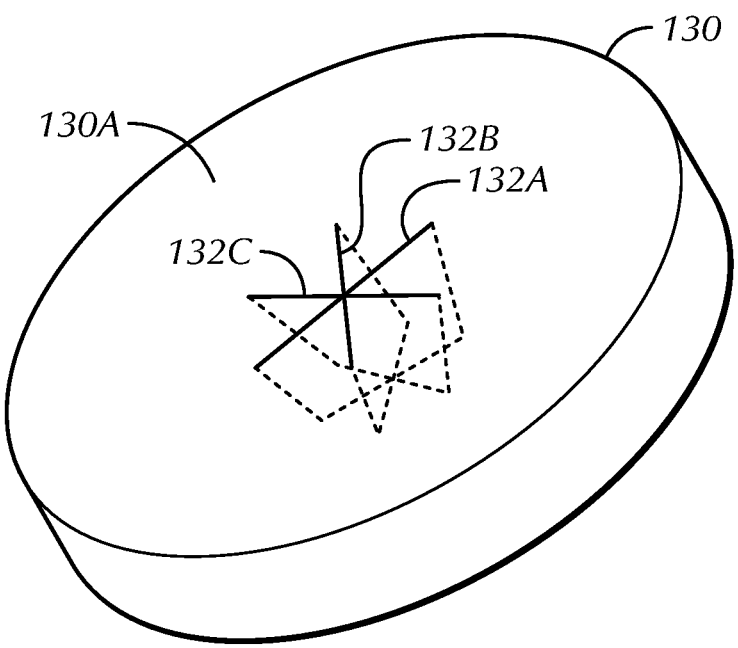
FIG. 3C

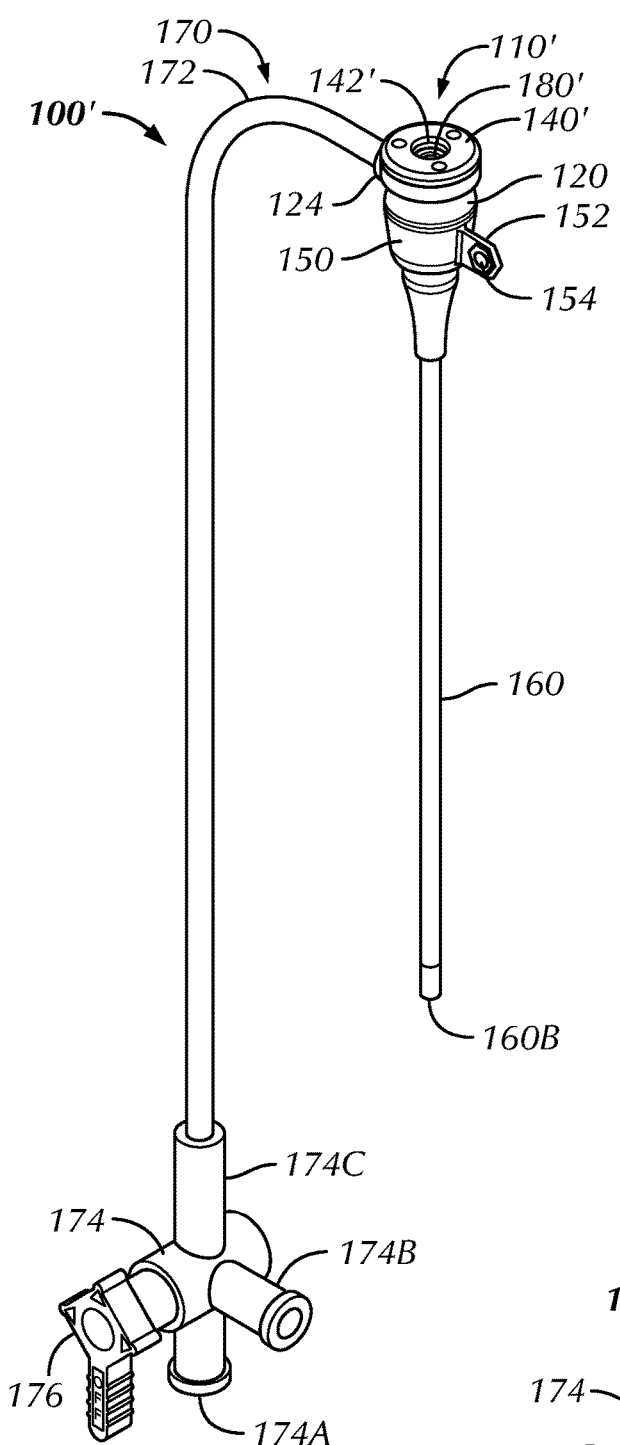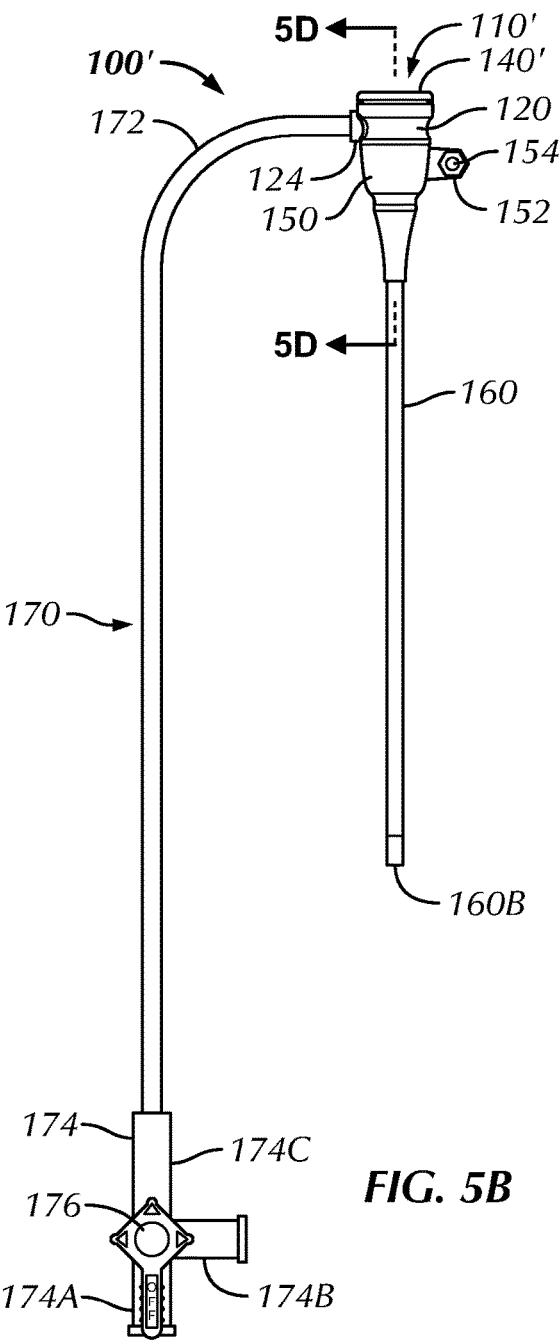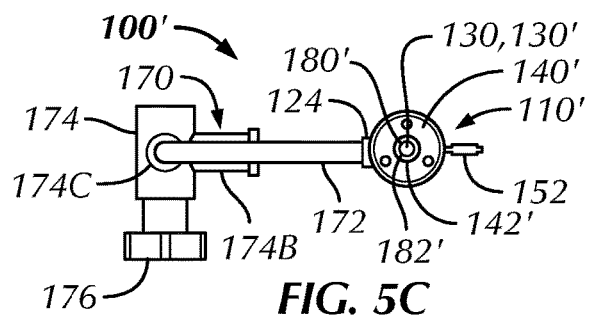
FIG. 5A
FIG. 5B
FIG. 5C

MEDICAL DEVICE WITH HEMOSTATIC VALVE

CROSS REFERENCE TO RELATED APPLICATIONS

This application claims the benefit of priority to U.S. Provisional Application Ser. No. 62/501,801, filed on May 5, 2017, entitled "CAP RETENTION FEATURES FOR HEMOSTATIC VALVE," and U.S. Provisional Application Ser. No. 62/501,876, filed on May 5, 2017, entitled "OVERMOLDED HUB ON EFEP," each of which is each incorporated by reference herein in its entirety.

BACKGROUND

The present invention relates to a medical device, and more specifically relates to a medical device including a hemostatic valve configured to inhibit fluid leakage from the medical device.

When inserting a device, such as a catheter, introducer, or other access device, within a patient, fluid of a higher pressure can be experienced within the patient, and in turn, the device, than is experienced in atmospheric conditions external to the device and the patient. This is particularly true with insertion of the device within an artery. Such a pressure differential can often lead to fluid leaking, spraying, or otherwise exiting from the device, which is typically not a desirable performance characteristic of such a device.

Overview

This overview is intended to provide an overview of subject matter of the present patent document. It is not intended to provide an exclusive or exhaustive explanation of the invention. The detailed description is included to provide further information about the present patent document.

The present inventors have recognized, among other things, that the present subject matter can be used to inhibit leakage from a medical device, such as, for instance, a catheter, a sheath, an introducer, or other access device. In various examples, the present subject matter is advantageous in that it provides increased responsiveness in sealing a hemostatic valve, thereby inhibiting spraying and excessive leaking from the valve. The present inventors have recognized the present subject matter can allow for a medical device including a thinner valve, thereby leading to reduced insertion force when inserting an instrument, device, or other object through the valve. Also, the present subject matter is advantageous in that it provides for improved manufacturing of a medical device including a hemostatic valve. To better illustrate the devices described herein, a non-limiting list of examples is provided here:

Example 1 can include subject matter that can include a hub for a medical device. The hub includes a hub housing including a passage from a proximal end of the hub housing to a distal end of the hub housing. A valve is disposed within the hub. The valve is configured to allow passage of an insertable device through the valve while inhibiting leakage of fluid from the valve. A cap is engaged to the hub housing. The cap includes an opening therethrough sized and shaped to allow passage of the insertable device through the opening. The opening allows access to the passage of the hub housing. An angled sidewall is disposed within the hub. The angled sidewall is configured to retain and deform the valve into a curved shape.

In Example 2, the subject matter of Example 1 is optionally configured such that the angled sidewall forms a tapered ring sized to accept the valve within the tapered ring.

In Example 3, the subject matter of Example 2 is optionally configured such that the tapered ring includes a first diameter at a proximal side of the tapered ring and a second diameter at a distal side of the tapered ring, the first diameter being smaller than the second diameter.

In Example 4, the subject matter of any one of Examples 1-3 is optionally configured such that the angled sidewall is configured to deform the valve into a substantially concave shape when viewed from a proximal side.

In Example 5, the subject matter of any one of Examples 1-4 is optionally configured such that the cap includes the angled sidewall.

In Example 6, the subject matter of any one of Examples 1-5 optionally includes a pressure ring disposed between the cap and the valve. The pressure ring includes a pressure ring opening that is smaller than the opening of the cap, wherein a distal side of the pressure ring is shaped to abut a first proximal side of the valve.

In Example 7, the subject matter of any one of Examples 1-6 is optionally combined with a sheath extending distally from the distal end of the hub housing. The sheath includes a lumen through the sheath. The lumen is fluidly coupled to the passage of the hub housing.

In Example 8, the subject matter of Example 7 is optionally configured such that the sheath is at least partially formed from EFEP.

In Example 9, the subject matter of any one of Examples 7-8 is optionally configured such that the sheath is overmolded with the hub housing.

Example 10 can include, or can optionally be combined with any one of Examples 1-9 to include subject matter that can include a medical device. A hub includes a hub housing including a passage from a proximal end of the hub housing to a distal end of the hub housing. A valve is disposed within the hub. The valve is configured to allow passage of an insertable device through the valve while inhibiting leakage of fluid from the valve. A cap is engaged to the hub housing. The cap includes an opening therethrough sized and shaped to allow passage of the insertable device through the opening. The opening allows access to the passage of the hub housing. An angled sidewall is disposed within the hub. The angled sidewall is configured to retain and deform the valve into a curved shape. A sheath extends distally from the distal end of the hub housing. The sheath includes a lumen through the sheath. The lumen is fluidly coupled to the passage of the hub housing.

In Example 11, the subject matter of Example 10 is optionally configured such that the angled sidewall forms a tapered ring sized to accept the valve within the tapered ring.

In Example 12, the subject matter of Example 11 is optionally configured such that the tapered ring includes a first diameter at a proximal side of the tapered ring and a second diameter at a distal side of the tapered ring, the first diameter being smaller than the second diameter.

In Example 13, the subject matter of any one of Examples 10-12 is optionally configured such that the angled sidewall is configured to deform the valve into a substantially concave shape when viewed from a proximal side.

In Example 14, the subject matter of any one of Examples 10-13 is optionally configured such that the cap includes the angled sidewall.

In Example 15, the subject matter of any one of Examples 10-14 is optionally configured such that the valve includes at least one slit within the valve. The slit extends from a first proximal side of the valve to a second distal side of the valve. The slit is angularly rotated within the valve from the first proximal side to the second distal side.

In Example 16, the subject matter of any one of Examples 10-15 is optionally configured such that the at least one slit includes at least two intersecting slits within the valve.

In Example 17, the subject matter of any one of Examples 10-16 is optionally configured such that the valve includes a first slit and a second slit. The first slit extends partially through the valve from a first proximal side of the valve. The second slit extends partially through the valve from a second distal side of the valve. The second slit is angularly offset from the first slit. The first and second slits intersect at a location within the valve intermediate the first proximal side and the second distal side.

In Example 18, the subject matter of any one of Examples 10-17 optionally includes a pressure ring disposed between the cap and the valve. The pressure ring includes a pressure ring opening that is smaller than the opening of the cap, wherein a distal side of the pressure ring is shaped to abut a first proximal side of the valve.

In Example 19, the subject matter of any one of Examples 10-18 is optionally configured such that the sheath is at least partially formed from EFEP.

In Example 20, the subject matter of any one of Examples 10-19 is optionally configured such that the sheath is overmolded with the hub housing.

BRIEF DESCRIPTION OF THE DRAWINGS

FIG. 1A is a perspective view of a medical device in accordance with at least one example of the invention.

FIG. 1B is a side view of a medical device in accordance with at least one example of the invention.

FIG. 1C is a top view of a medical device in accordance with at least one example of the invention.

FIG. 3A is a top view of a valve of a medical device in accordance with at least one example of the invention.

FIG. 3B is a side view of a valve of a medical device in accordance with at least one example of the invention.

FIG. 3C is a perspective view of a valve of a medical device in accordance with at least one example of the invention.

FIG. 5A is a perspective view of a medical device in accordance with at least one example of the invention.

FIG. 5B is a side view of a medical device in accordance with at least one example of the invention.

FIG. 5C is a top view of a medical device in accordance with at least one example of the invention.

DETAILED DESCRIPTION

The present patent application relates to a medical device, and more specifically relates to a medical device including a valve configured to inhibit fluid leakage from the medical device. In various examples, as described herein, the medical device can include various introducers, catheters, sheaths, and/or other access devices including a hemostatic valve configured to allow insertion of a device, instrument, or other object through the valve while inhibiting fluid leakage from the valve.

Figure 1D:
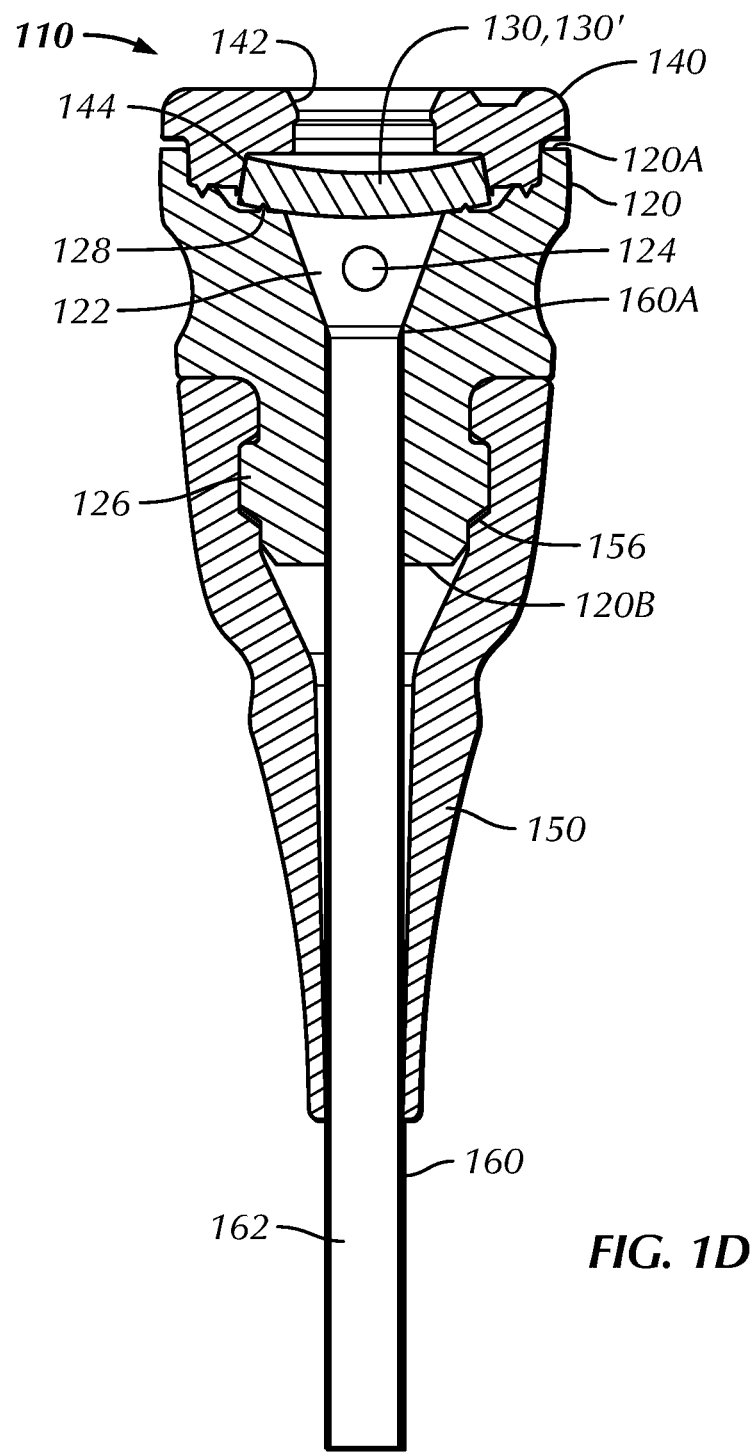
FIG. 1D is a cross-sectional view of the medical device of FIG. 1B taken along line 1D-1D.
Figure 5D:
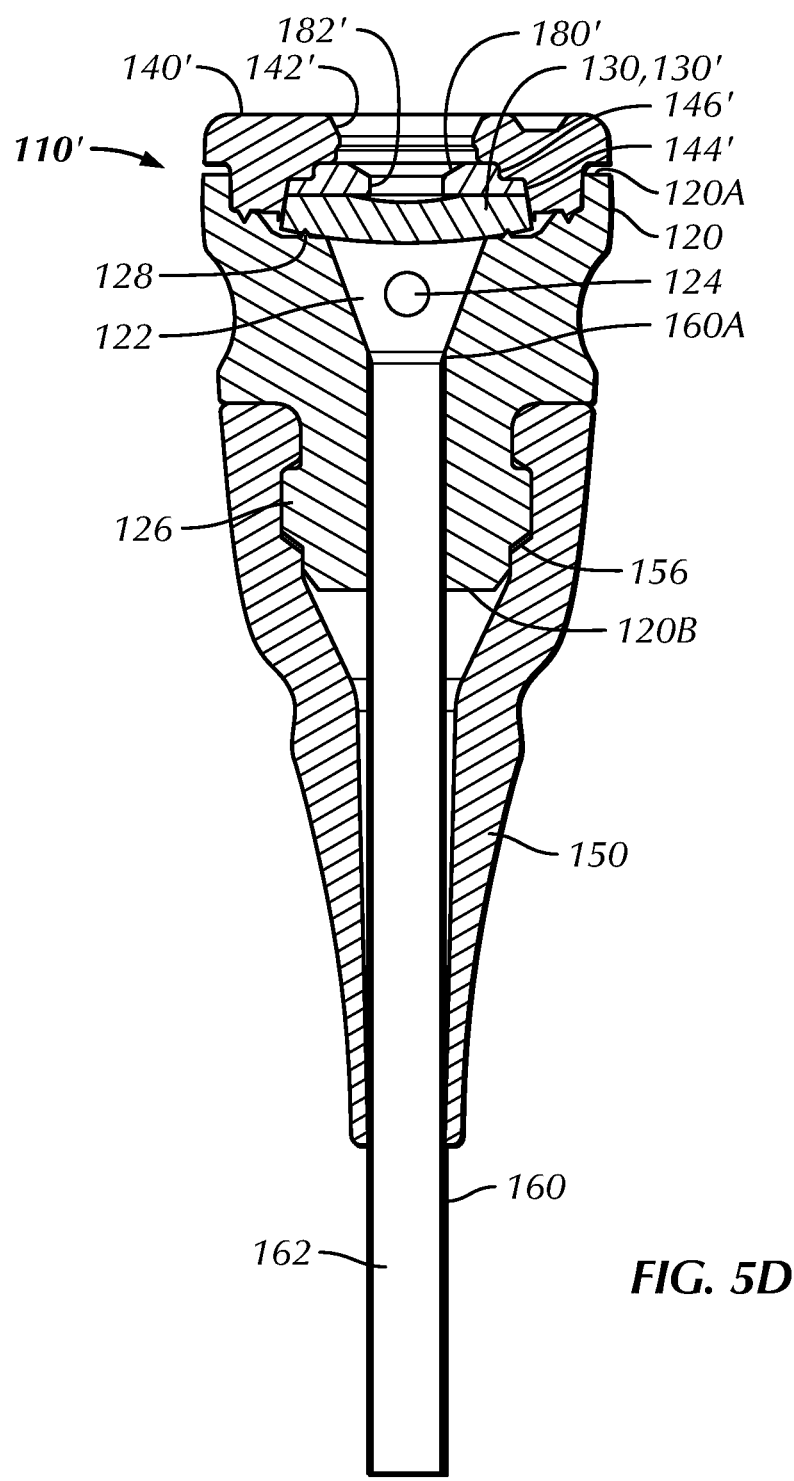
FIG. 5D is a cross-sectional view of the medical device of FIG. 5B taken along line 5D-5D.

Referring to FIGS. 1A-1D and 5A-5D, in various examples, a medical device 100, 100' includes a hemostatic valve in order to inhibit, if not eliminate, fluid leakage from the medical device 100, 100', for instance, when the medical device 100, 100' is at least partially inserted within a patient. In some examples, the medical device 100, 100' is configured to inhibit fluid leakage from the medical device 100, 100' with the medical device 100, 100' at least partially inserted within vasculature of the patient. In further examples, the medical device 100, 100' is configured to inhibit fluid leakage from the medical device 100, 100' with the medical device 100, 100' at least partially inserted within an artery of the patient. In various examples, the medical device 100, 100' includes an introducer, a sheath, a catheter, or other access device. In other examples, the medical device 100, 100' can include any device for which a pressure differential is present between inside of the medical device 100, 100' and outside of the medical device 100, 100', for instance, when the medical device 100, 100' is at least partially inserted within the patient.

The example medical devices 100, 100' shown in FIGS. 1A-1D and 5A-5D include introducers which are each shown as including a side port 170. The side port 170, in some examples, allows for introduction of a fluid, such as saline, for instance, into the medical device 100, 100'. In other examples, a gas can be introduced into the medical device 100, 100' using the side port 170. In some examples, a pressure source can be fluidly coupled to the medical device 100, 100' using the side port 170. In some examples, a negative pressure can be introduced to the medical device 100, 100' using the side port 170, for instance to suction or otherwise remove fluid, gas, or other materials from within the medical device 100, 100' and/or the patient. In other examples, a positive pressure can be introduced to the medical device 100, 100' using the side port 170, for instance to inflate a cavity of the patient.

In some examples, the side port 170 includes a tube 172 or other conduit fluidly coupled to a hub 110, 110' of the medical device 100, 100' at a side port opening 124. In some examples, the side port includes a stopcock 174 or other valve configured to allow fluid coupling of one or more inlets 174A, 174B to an outlet 174C of the stop cock 174. Although shown with two inlets 174A, 174B, in other examples, the stopcock 174 can include fewer or more than two inlets 174A, 174B, depending on the desired application and/or requirements for the procedure to be performed using the medical device 100, 100'. The outlet 174C, in some examples, is fluidly coupled to the tube 172 or other conduit. In some examples, the stopcock 174 includes a handle 176 that is rotatable or otherwise actuatable in order to fluidly couple one or more of the inlets 174A, 174B to the outlet 174C and, in turn, the hub 110, 110' of the medical device 100, 100'. In this way, a fluid source and/or a pressure source can be coupled to one or more of the inlets 174A, 174B with the handle 176 being used to select which, if any, of the one or more inlets 174A, 174B to fluidly couple with the hub 110, 110' of the medical device 100, 100'. Although shown as including the side port 170, this is not intended to be limiting. That is, in some examples, the present subject matter can be used with a medical device that does not include a side port. While various exemplary devices are shown and described herein, these are merely exemplary and should not be considered limiting.

Referring now to FIGS. 1A-1D, in some examples, the medical device 100 includes the hub 110. In some examples, the hub 110 includes a hub housing 120 including a passage 122 from a proximal end 120A of the hub housing 120 to a distal end 120B of the hub housing 120. In some examples, the hub housing 120 includes the side port opening 124 for attachment to the tube 172 or other conduit of the side port 170. In some examples, the side port opening 124 is fluidly coupled to the passage 122 within the hub housing 120. In some examples, the hub 110 includes a valve 130, 130' disposed within the hub 110. The valve 130, 130', which is described in greater detail below, is configured, in some examples, to allow passage of an insertable device through the valve 130, 130' while inhibiting leakage of fluid from the valve 130, 130'. In various examples, various insertable devices are contemplated for use with the medical device 100, including, but not limited to, a guidewire, a catheter, an introducer, a sheath, a dilator, or other instrument, tool, or device. In some examples, a cap 140 is engaged to the hub housing 120. In some examples, the cap 140 includes an opening 142 therethrough sized and shaped to allow passage of the insertable device through the opening 142. In some examples, the opening 142 allows access to the passage 122 of the hub housing 120, such that, with insertion of the insertable device through the opening 142 of the cap 140, the insertable device can be further moved distally to enter the passage 122 within the hub housing 120. An angled sidewall 144, in some examples, is disposed within the hub 110, the angled sidewall 144 being configured to retain and deform the valve 130, 130' into a curved shape.

In some examples, the cap 140 and the hub housing 120 of the hub 110 are each formed from a polymeric material. In some examples, the cap 140 and the hub housing 120 can be formed from the same material, while, in other examples, the cap 140 and the hub housing 120 can be formed from different materials. In some examples, the cap 140 and/or the hub housing 120 are/is formed from nylon. In other examples, the cap 140 and/or the hub housing 120 are/is formed from acrylonitrile-butadiene-styrene (ABS).

In some examples, a sheath 160 extends distally from the distal end 120B of the hub housing 120. The sheath 160, in some examples, includes a lumen 162 through the sheath 160. In some examples, the lumen 162 is fluidly coupled to the passage 122 of the hub housing 120. In this way, an insertable device can be passed through the valve 130, 130', into the passage 122, through the lumen 162, and out of a distal end 160B of the sheath 160 in order to access a location within the patient with the insertable device. In some examples, the sheath 160 includes a proximal end 160A that is partially disposed within the passage 122 of the hub housing 120. In some examples, the sheath 160 is overmolded with the hub housing 120. In further examples, the hub housing 120 is overmolded to the proximal end 160A of the sheath 160. In some examples, the sheath 160 is at least partially formed from ethylene-tetrafluoroethylene-hexafluoropropylene-fluoroterpolymer (EFEP). In some examples, the hub housing 120 is at least partially formed from nylon. In some examples, the hub housing 120 is at least partially formed from acrylonitrile-butadiene-styrene (ABS). In some examples, the EFEP material includes properties that facilitate overmolding of the EFEP material and the hub housing 120. That is, a relatively low processing temperature of the EFEP material allows for increased adhesion when overmolded. In some examples, the melting temperature of the EFEP material is significantly lower than other materials contemplated for use in forming the tubing, such as, but not limited to, fluorinated ethylene propylene (FEP) and ethylene tetrafluoroethylene (ETFE).

In some examples, EFEP can include mechanical properties that are desirable for the manufacture and/or function of the medical device 100. In some examples, the use of EFEP for the sheath 160 allows for simpler and cheaper processes to produce the medical device 100, leading to decreased manufacture time and expense than would otherwise be expected with a medical device formed using a material other than EFEP for a sheath. In some examples, the use of EFEP gives flexibility and column strength similar to that of FEP or ETFE but lower melting characteristics lends to better adhesion when overmolded.

In some examples, the medical device 100 includes the sheath 160 formed from EFEP, the sheath 160 being etched at the proximal end 160A and overmolded with the hub housing 120. In some examples, the EFEP of the sheath 160 can be chemically etched to improve and/or strengthen bonding between the sheath 160 and the hub housing 120, for instance, to increase tensile and liquid performance. In some examples, the EFEP of the sheath 160 includes a sodium napthalene chemical etch. In some examples, the sheath 160 can be overmolded to the hub housing 120 without the sheath 160 being etched. In some examples, the sheath 160 can include a thermoformed tip at the distal end 160B. In some examples, a length of the sheath 160 can be coated with a lubricious hydrophilic coating.

In some examples, the sheath 160, for instance, formed from EFEP, can be formed with a relatively thin wall, due to, at least in part, mechanical properties of the EFEP material, such as, but not limited to, column strength and kink properties. In some examples, the sheath 160 can be formed with a wall thickness of 0.010 inches or less. In further examples, the sheath 160 can be formed with a wall thickness of 0.005 inches. Having a thinner wall, in some examples, allows for a reduction in outer diameter of the sheath 160 while still maintaining an inner diameter sufficient to pass various insertable devices, including, but not limited to instruments, devices, or the like, through the medical device 100. This allows for a physician or other user to make a smaller incision in the patient receiving the medical device 100, thereby allowing for an easier and/or less traumatic experience for the patient. In some examples, the sheath 160 formed from EFEP can allow for the sheath 160 of the medical device 100 to include an outer diameter that is similar to other introducers but with a larger inner diameter, thereby allowing for larger insertable devices, instruments, or other devices to be passed through the medical device 100.

In some examples, the medical device 100 includes a strain relief member 150 configured to reduce kinking, tearing, and/or excessive bending of the sheath 160, particularly in the area of where the sheath 160 extends from the hub housing 120. In some examples, the strain relief member 150 is configured to limit the amount of bending of the sheath 160 proximate to the hub housing 120. In some examples, the strain relief member 150 allows for flexibility in the sheath 160 while minimizing stress on the sheath 160, particularly in the area of the sheath 160 proximate where the sheath 160 extends from the hub housing 120, which is oftentimes a location of the sheath 160 that is vulnerable to excessive bending, kinking, and/or tearing or other breakage. In some examples, the strain relief member 150 includes a resilient material. In further examples, the strain relief member 150 is formed from one or more resilient materials. For instance, in some examples, the strain relief member 150 is at least partially formed from a thermoplastic elastomer (TPE).

In some examples, the strain relief member 150 is engageable with the hub housing 120. In some examples, the strain relief member 150 is rotatably engageable with the hub housing 120. In various examples, the strain relief member 150 can be engaged with the hub housing 120 in different ways, including, but not limited to, a snap fit, a frictional engagement, being attached with adhesive, being attached with one or more fasteners, a bayonet connection, a tab-in-slot connection, or a combination thereof. For instance, in the example shown in FIG. 1D, the strain relief member 150 is snap fit to the hub housing 120. In this example, the hub housing 120 includes a ridge 126 proximate the distal end 120B of the hub housing 120, and the strain relief member 150 includes a channel 156 sized and shaped to accept the ridge 126 of the hub housing within the channel 156. In some examples, the resilient nature of the strain relief member 150 allows for the strain relief member 150 to temporarily deform to allow the strain relief member 150 to be passed over the ridge 126 of the hub housing 120 to place the ridge 126 within the channel 156 of the strain relief member 150, thereby attaching the strain relief member 150 to the hub housing 120. In some examples, the strain relief member 150 is formed from a material that is soft to the touch. In some examples, the strain relief member 150 is rotatable with respect to the hub housing 120. For instance, in some examples, the strain relief member 150 can be relatively loosely attached to the hub housing 120 to allow for the strain relief member 150 to rotate with respect to the hub housing 120. In other examples, however, the strain relief member 150 can be relatively tightly attached to the hub housing 120, thereby inhibiting rotation of the strain relief member 150, if desired.

In some examples, the strain relief member 150 includes a tab 152 extending outwardly from the strain relief member 150. In further examples, the tab 152 can include a suture hole 154 through the tab to allow for the medical device 100 to be attached to the patient and/or another object using one or more sutures through the suture hole 154. In some examples, it can be desirable for the strain relief member 150 to be rotatable with respect to the hub housing 120 to allow for rotation of the tab 152 and, in turn, the suture hole 154, to allow for adjustment of the tab 152 and the suture hole 154 for proper positioning of the suture hole 154 with respect to the patient and/or other object prior to suturing of the medical device 100 to the patient and/or other object.

Figure 2A:
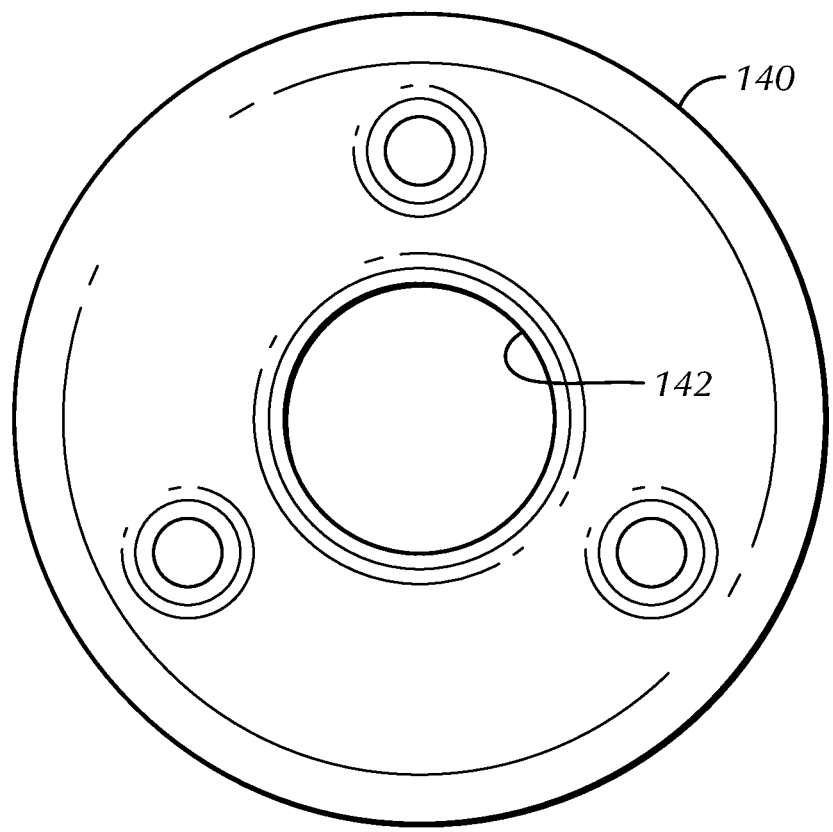
FIG. 2A is a top view of a cap of a medical device in accordance with at least one example of the invention.
Figure 2C:
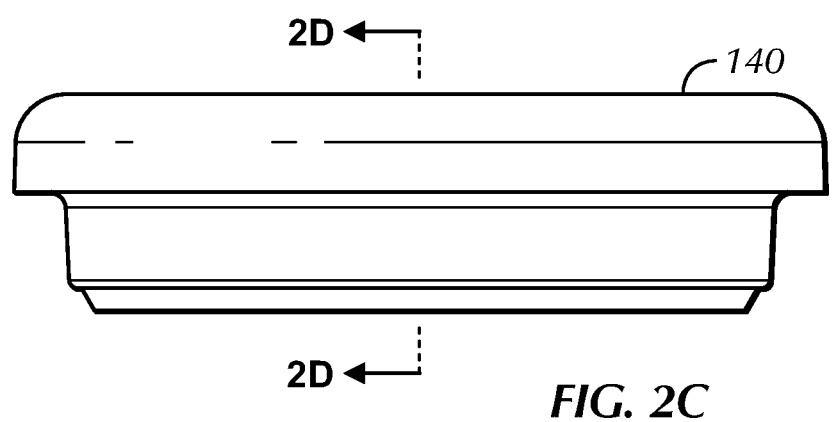
FIG. 2C is a side view of a cap of a medical device in accordance with at least one example of the invention.
Figure 2B:
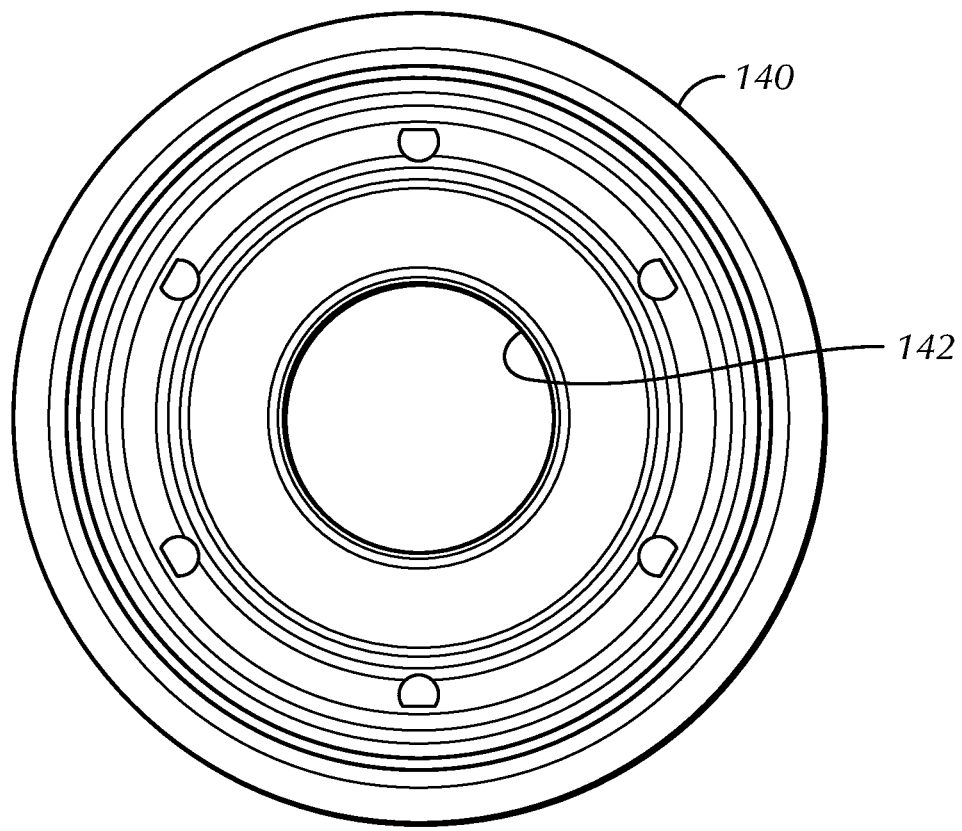
FIG. 2B is a bottom view of a cap of a medical device in accordance with at least one example of the invention.
Figure 2D:
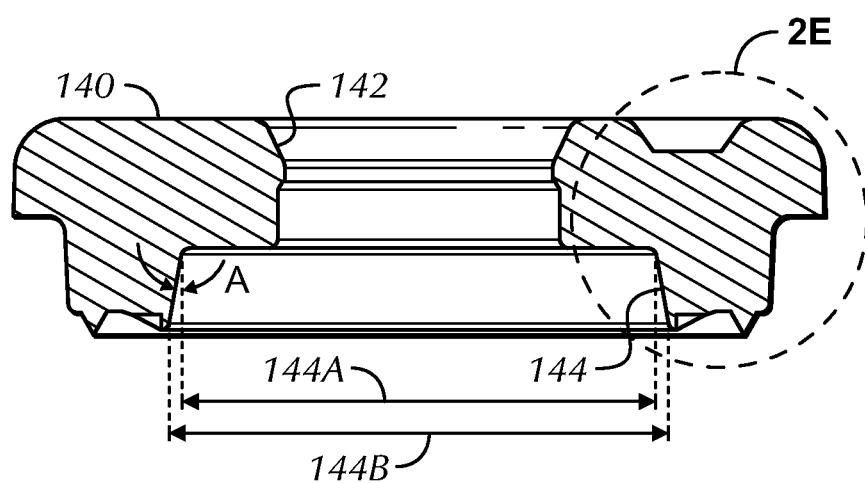
FIG. 2D is a cross-sectional view of the cap of FIG. 2C taken along line 2D-2D.
Figure 2E:
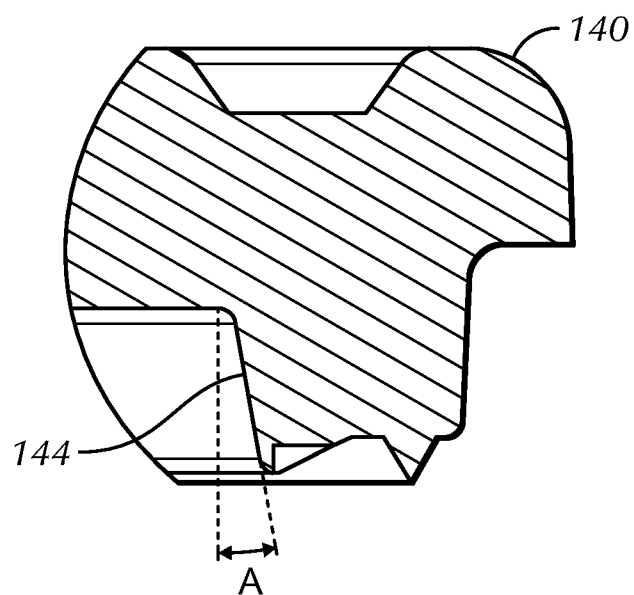
FIG. 2E is an enlarged view of a portion 2E of the cap of FIG. 2D.
Figure 2F:
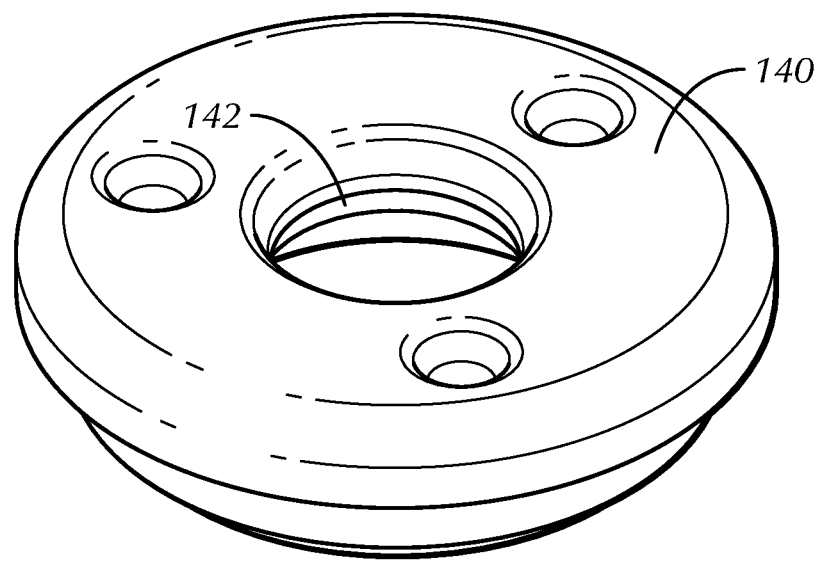
FIG. 2F is a perspective view of a cap of a medical device in accordance with at least one example of the invention.

Referring now to FIGS. 1A-2F, the medical device 100 includes the angled sidewall 144 configured to accept and retain the valve 130, 130' within the angled sidewall 144. In some examples, the angled sidewall 144 can include discrete segments formed around the area within which the valve 130, 130' is to be positioned. In other examples, the angled sidewall 144 forms a tapered ring sized to accept the valve 130, 130' within the tapered ring. In some examples, the cap 140 includes the angled sidewall 144. In some examples, the angled sidewall 144 is integrally formed as part of the cap 140. In other examples, the hub housing can include the angled sidewall.

In some examples, the angled sidewall 144 is configured to compress the valve 130, 130' in order to retain the valve 130, 130' within the angled sidewall 144, effectively pinching the valve 130, 130' within the angled sidewall 144. In some examples, the tapered ring formed by the angled sidewall 144 includes a first diameter 144A at a proximal side of the tapered ring and a second diameter 144B at a distal side of the tapered ring. In some examples, the first diameter 144A is smaller than the second diameter 144B. In other examples, the first diameter 144A is substantially equal to the second diameter 144B. In some examples, the angled sidewall 144 provides radial compression on the valve 130, 130'. Such radial compression improves the response of the valve 130, 130' to close upon removal of an insertable device from the valve 130, 130'.

In some examples, the angled sidewall is at an angle A from vertical in the range of 0 degrees to 45 degrees. In some examples, the angle A of the angled sidewall 144 is angled at about 10 degrees from vertical. With the valve 130, 130' disposed within the angled sidewall 144, in some examples, the angled sidewall 144 causes the valve 130, 130' to deform into a substantially concave shape when viewed from a proximal side (see FIG. 1D). That is, a center of the valve 130, 130' extends more distally than an outside edge of the valve 130, 130'. In other examples, the angled sidewall 144 can be configured to cause the valve 130, 130' to deform the valve 130, 130' into a substantially convex shape when viewed from the proximal side. For instance, in order to achieve a substantially convex shape of the valve 130, 130' when viewed from a proximal side, the angled sidewall 144 can be configured such that the first diameter 144A is larger than the second diameter 144B. In still further examples, the angled sidewall 144 can be configured to cause the valve 130, 130' to remain substantially flat rather than forming a concave shape or a convex shape when viewed from the proximal side. For instance, in order to achieve a substantially flat shape of the valve 130, 130', the angled sidewall 144 can be configured such that the angle A from vertical is substantially 0 degrees.

In some examples, with the angled sidewall 144 included with the cap 140, the valve 130, 130' can be placed and retained within the cap 144 prior to attaching the cap 140 to the hub housing 120. In some examples, the angled sidewall can be included with the hub housing 120, in which case, the valve 130, 130' can be inserted within the angled sidewall of the hub housing 120 prior to attachment of the cap 140 to the hub housing 120. In some examples, with the cap 140 attached to the hub housing 120, the valve 130, 130' is compressed between the cap 140 and the hub housing 120 to aid in retaining the valve 130, 130' in place within the medical device 100. For instance, retention of the valve 130, 130' within the angled sidewall 144 and/or compression of the valve 130, 130' between the cap 140 and the hub housing 120 can aid in retaining the valve 130, 130' in place within the medical device 100 while the insertable device is passed through the valve 130, 130'; while the insertable device is manipulated, positioned, or otherwise used within the patient; and/or while the insertable device is removed from the patient, the valve 130, 130', and/or the medical device 100. In some examples, insertion of the insertable device through the valve 130, 130' can cause a distally-directed force on the valve 130, 130', which, in turn, can tend to pull the outer edge of the valve 130, 130' toward the center of the valve 130, 130'. By compressing the valve 130, 130' between the cap 140 and the hub housing 120, in some examples, the outer edge of the valve 130, 130' can be inhibited from pulling away from the angled sidewall 144 and toward the center of the valve 130, 130', thereby maintaining the valve 130, 130' in place within the medical device 100.

In some examples, the hub housing 120 includes a tooth 128 (FIG. 1D) or other projection extending from a surface of the hub housing 120 and configured to bear into the valve 130, 130' with compression of the valve 130, 130' between the cap 140 and the hub housing 120. In this way, a stress concentration is created in the valve 130, 130' to aid in retaining the valve 130, 130' in position within the medical device 100. In some examples, the tooth 128 is annularly-shaped, extending around the entire passage 122 of the hub housing 120. In other examples, the tooth 128 can be made up of two or more discrete segments extending around the passage 122 of the hub housing 120. Although the tooth 128 is shown as being substantially triangular in shape in cross section, in other examples, other cross-sectional shapes of the tooth 128 are contemplated, including, but not limited to, rectangular, rounded, saw-tooth-patterned, or the like. Although the tooth 128 is shown extending from the hub housing 120, in other examples, it is contemplated that the tooth extends from the cap 140. Such a configuration, in some examples, can be particularly well-suited for use with the valve deformed into the substantially convex shape when viewed from the proximal side. In further examples, each of the hub housing 120 and the cap 140 can include a tooth or other protrusion to increase compression of the valve 130, 130' between the cap 140 and the hub housing 120 and aid in maintaining the valve 130, 130' in position within the medical device 100.

In some examples, the cap 140 is attached to the hub housing 120. In some examples, the cap 140 is attached to the hub housing 120 in a manner to inhibit the removal of the cap 140 from the hub housing, thereby helping to maintain the integrity of the medical device 100 and the fitness of the medical device 100 for use, for instance, in a procedure. In some examples, the cap 140 can be welded to the hub housing 120. In further examples, the cap 140 can be sonically welded to the hub housing 120. In various other examples, the cap 140 can be attached to the hub housing 120 in various other ways, including, but not limited to, the cap 140 being frictionally engaged, snap fit, adhesively attached, and/or attached using one or more fasteners to the hub housing 120.

In some examples, the medical device 100 provides a complete seal around the valve 130, 130'. That is, in some examples, the cap 140 is attached to the hub housing 120 (in some examples, by sonic welding, although other methods of attachment are contemplated herein) with the valve 130, 130' compressed within the angled sidewall 144, thereby axially compressing the valve 130, 130' between the cap 140 and the hub housing 120. The tooth 128, in some examples, provides a concentrated axial force against the bottom of the valve 130, 130'. In this way, the radial compression of the valve 130, 130' provided by the angled sidewall 144, the axial compression of the valve 130, 130' caused by the attachment of the cap 140 to the hub housing 120, and/or the concentrated axial force on the bottom of the valve 130, 130' provided by the tooth 128 contribute to providing a hemostatic seal for the medical device 100.

Referring to FIGS. 3A-3C, in some examples, the medical device 100 can include the valve 130 disposed within the medical device 100 (see FIGS. 1A-1D). In some examples, the valve 130 includes a shape complementary to the shape of the angled sidewall 144 within which the valve 130 is to be disposed. In some examples, the valve 130 includes a substantially circular shape when viewed from above or below. However, the shape of the valve 130 is not intended to be limiting and the valve 130 can take other shapes provided the valve 130 is capable of fitting and properly functioning within the medical device 100. In some examples, the valve 130 includes at least one slit 132A within the valve 130. In some examples, the slit 132A extends from a first proximal side 130A of the valve 130 to a second distal side 130B of the valve 130. In some examples, the slit 132A is angularly rotated within the valve 130 from the first proximal side 130A to the second distal side 130B. That is, the slit 132A begins on the first proximal side 130A of the valve 130 at a first angular position with respect to the valve 130 and ends on the second distal side 130B of the valve 130 at a second angular position that is different from the first angular position. As seen in FIG. 3A, one end of the slit 132A is rotationally offset from the other end of the slit 132A. Stated in another way, in some examples, the one or more slits 132A of the valve 130 are spirally disposed within the valve 130. In other examples, however, it is contemplated that the one or more slits include no angular rotation, such that the one or more slits pass straight through the valve.

In some examples, the valve 130 includes two or more slits 132A, 132B within the valve 130. In further examples, each of the at least two slits 132A, 132B is angularly rotated within the valve 130 from one end of the slit 132A, 132B to the other end of the slit 132A, 132B. In some examples, the at least two slits 132A, 132B intersect. In further examples, the at least two slits 132A, 132B intersect at a center of the valve 130. In other examples, it is contemplated the at least two slits intersect in a location within the valve other than the center of the valve. In further examples, the valve 130 includes a third slit 132C in addition to the slits 132A, 132B. In some examples, each of the slits 132A, 132B, 132C is angularly rotated within the valve 130 from one end of the slit 132A, 132B, 132C to the other end of the slit 132A, 132B, 132C. In some examples, the slits 132A, 132B, 132C intersect. In further examples, the slits 132A, 132B, 132C intersect at a center of the valve 130. In other examples, it is contemplated that the slits intersect in a location within the valve other than the center of the valve. In still further examples, it is contemplated that the valve includes more than three slits. The number of slits included in the valve can depend on various factors including, but not limited to, pressure requirements, force needed to pass an insertable instrument through the valve, size of the valve, and/or material of the valve. As such, it is contemplated that the valve 130 includes any number of slits 132A, 132B, 132C, provided the valve 130 is capable of properly functioning within the medical device 100.

Figure 4A:
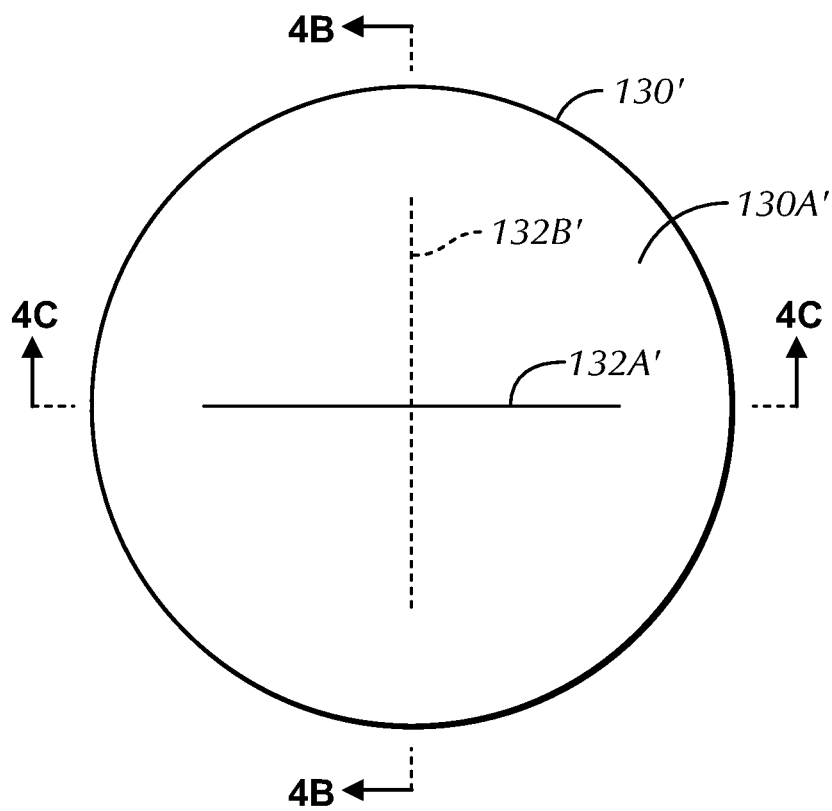
FIG. 4A is a top view of a valve of a medical device in accordance with at least one example of the invention.
Figure 4B:
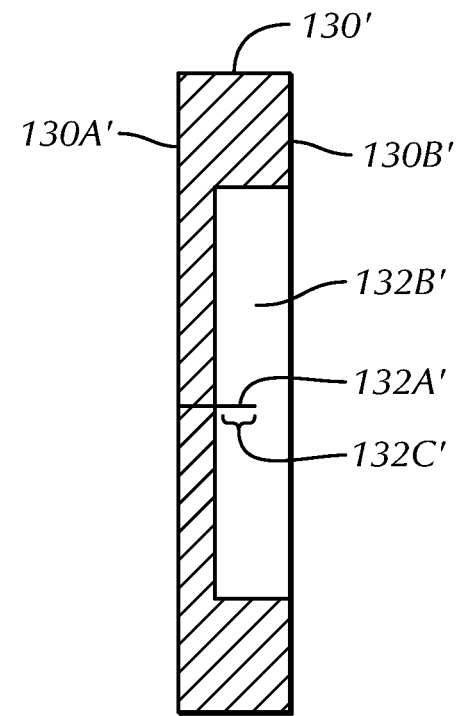
FIG. 4B is a cross-sectional view of the valve of FIG. 4A taken along line 4B-4B.
Figure 4C:
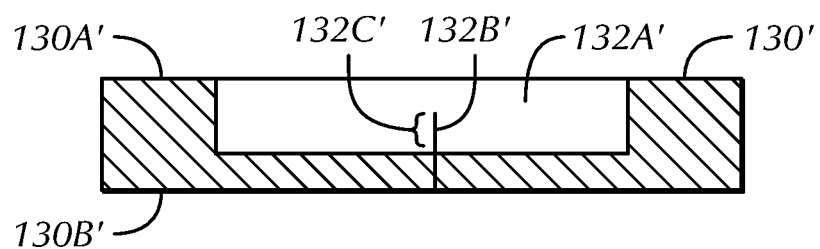
FIG. 4C is a cross-sectional view of the valve of FIG. 4A taken along line 4C-4C.
Figure 4D:
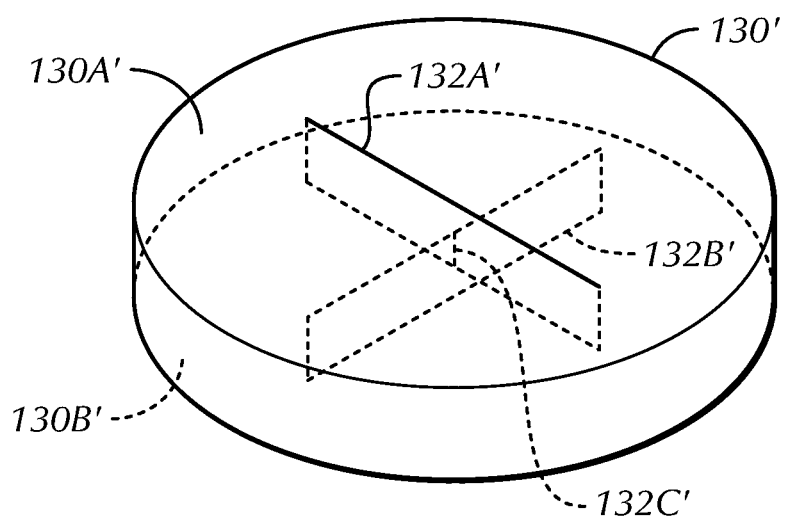
FIG. 4D is a perspective view of a valve of a medical device in accordance with at least one example of the invention.

Referring to FIGS. 4A-4D, in some examples, the medical device 100 can include the valve 130' disposed within the medical device 100 (see FIGS. 1A-1D). In some examples, the valve 130' includes a shape complementary to the shape of the angled sidewall 144 within which the valve 130' is to be disposed. In some examples, the valve 130' includes a substantially circular shape when viewed from above or below. However, the shape of the valve 130' is not intended to be limiting and the valve 130' can take other shapes provided the valve 130' is capable of fitting and properly functioning within the medical device 100. In some examples, the valve 130' can include two or more crossed slits 132A', 132B', each extending through at least a portion of the thickness of the valve 130'. That is, in some examples, the valve 130' includes a first slit 132A' extending partially through the valve from a first proximal side 130A' of the valve 130' and a second slit 132B' extending partially through the valve 130' from a second distal side 130B' of the valve 130'. In some examples, the second slit 132B' is angularly offset from the first slit 132A'. In some examples, the first slit 132A' is angularly offset from the second slit 132B' by substantially 90 degrees. In other examples, the first and second slits 132A', 132B' can be angularly offset by less than 90 degrees. In some examples, the first and second slits 132A', 132B' intersect at a location 132C' within the valve 130 intermediate the first proximal side 130A and the second distal side 130B.

In various examples, various materials are contemplated for use in the valve 130, 130'. In some examples, the valve 130, 130' can be at least partially formed from an elastomer. In some examples, the valve 130, 130' can be at least partially formed from a silicone material. In some examples, the valve 130, 130' can be at least partially formed from a high consistency rubber (HCR) silicone. In further examples, the silicone material of the valve 130, 130' can include a liquid silicone lubricant. In some examples, the valve 130, 130' can be formed from a liquid silicone infused HCR material. In some examples, the valve 130, 130' can include a radiopacifier additive to allow for the valve 130, 130' to include at least some radiopaque characteristics. In other examples, one or more other materials can be used to form the valve 130, 130' depending upon various factors, including, but not limited to, pressure differential between ambient pressure and pressure within the patient; environmental conditions; fluid(s) involved; size of the valve 130, 130' and/or the medical device 100; thickness of the valve 130, 130'; and/or type of insertable device to be passed through the valve 130, 130'.

In various examples, various types of valves are contemplated for use within the medical device 100, including, but not limited to, the valve 130 (FIGS. 3A-3C) and the valve 130' (FIGS. 4A-4D). As such, although the valves 130, 130' are described in detail herein, it is contemplated that valves other than those described herein can be used within the medical device 100 and the present subject matter should not be limited to only the medical device 100 including the valve 130, 130' described herein. That is, in some examples, the medical device 100 of the present subject matter is independent of valve design, and, more specifically, valve slit design.

Referring now to FIGS. 5A-5D, in some examples, the medical device 100' is, in many ways, substantially similar to the medical device 100 described above, with substantially similar components or aspects having the same reference numbers as those described with respect to the medical device 100. For that reason, the following description of the medical device 100' is limited to the differences between the medical device 100 and the medical device 100', with reference numbers of different components or aspects being denoted with a prime ('), except for the valve 130'. In a similar manner to that described above with respect to the medical device 100, either the valve 130 or the valve 130' can be used with the medical device 100'. It should be understood that all of the benefits and advantages described above with respect to the medical device 100 apply equally with respect to the medical device 100'.

In some examples, the medical device 100' includes the hub 110'. In some examples, the hub 110' includes the hub housing 120 including the passage 122 from the proximal end 120A of the hub housing 120 to the distal end 120B of the hub housing 120. In some examples, the hub housing 120 includes the side port opening 124 for attachment to the tube 172 or other conduit of the side port 170. In some examples, the side port opening 124 is fluidly coupled to the passage 122 within the hub housing 120. In some examples, the hub 110' includes the valve 130, 130' disposed within the hub 110'. The valve 130, 130' is configured, in some examples, to allow passage of an insertable device through the valve 130, 130' while inhibiting leakage of fluid from the valve 130, 130'. In various examples, various insertable devices are contemplated for use with the medical device 100', including, but not limited to, a guidewire, a catheter, an introducer, a sheath, a dilator, or other instrument, tool, or device. In some examples, a cap 140' is engaged to the hub housing 120. In some examples, the cap 140' includes an opening 142' therethrough sized and shaped to allow passage of the insertable device through the opening 142'. In some examples, the opening 142' allows access to the passage 122 of the hub housing 120, such that, with insertion of the insertable device through the opening 142' of the cap 140', the insertable device can be further moved distally to enter the passage 122 within the hub housing 120. An angled sidewall 144', in some examples, is disposed within the hub 110, the angled sidewall 144' being configured to retain and deform the valve 130, 130' into a curved shape.

In some examples, the cap 140' and the hub housing 120 of the hub 110' are each formed from a polymeric material. In some examples, the cap 140' and the hub housing 120 can be formed from the same material, while, in other examples, the cap 140' and the hub housing 120 can be formed from different materials. In some examples, the cap 140' and/or the hub housing 120 are/is formed from nylon. In other examples, the cap 140' and/or the hub housing 120 are/is formed from ABS.

Figure 6A:
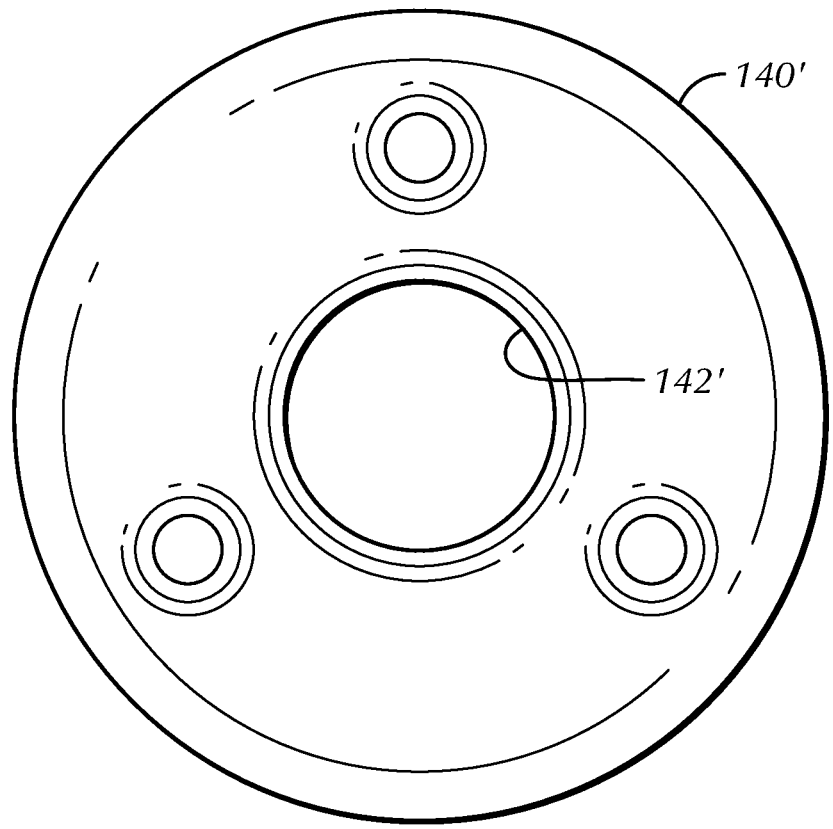
FIG. 6A is a top view of a cap of a medical device in accordance with at least one example of the invention.
Figure 6C:
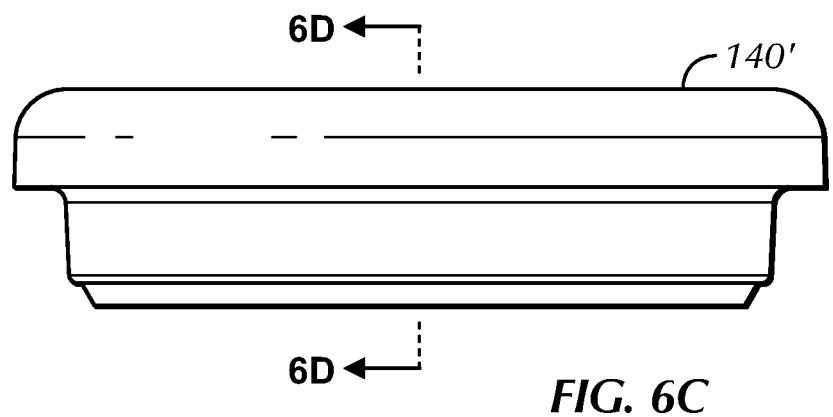
FIG. 6C is a side view of a cap of a medical device in accordance with at least one example of the invention.
Figure 6B:
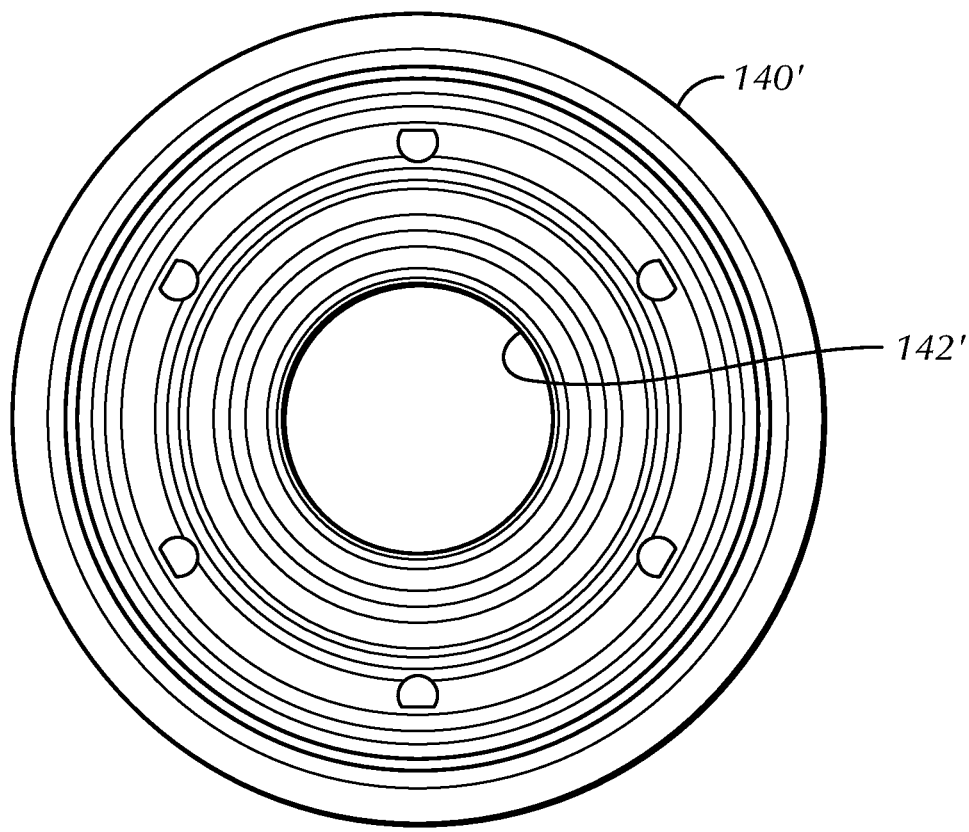
FIG. 6B is a bottom view of a cap of a medical device in accordance with at least one example of the invention.
Figure 6D:
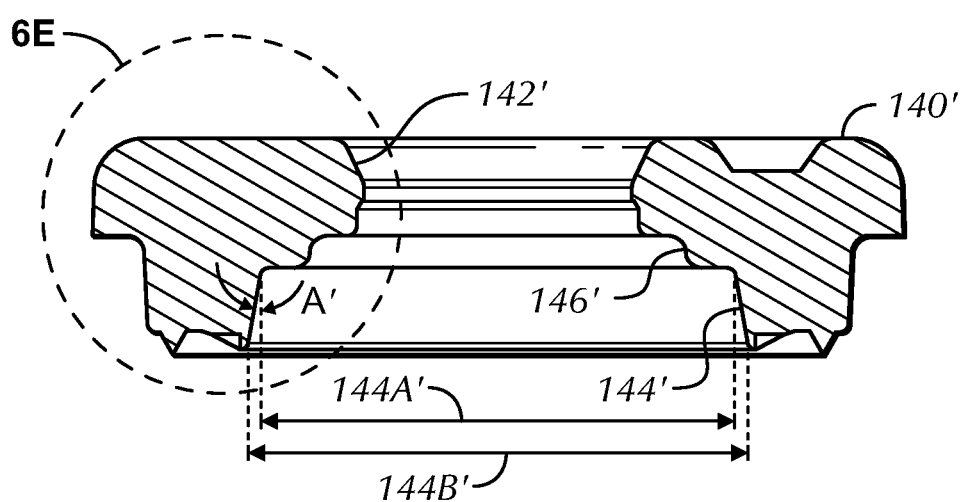
FIG. 6D is a cross-sectional view of the cap of FIG. 6C taken along line 6D-6D.
Figure 6E:
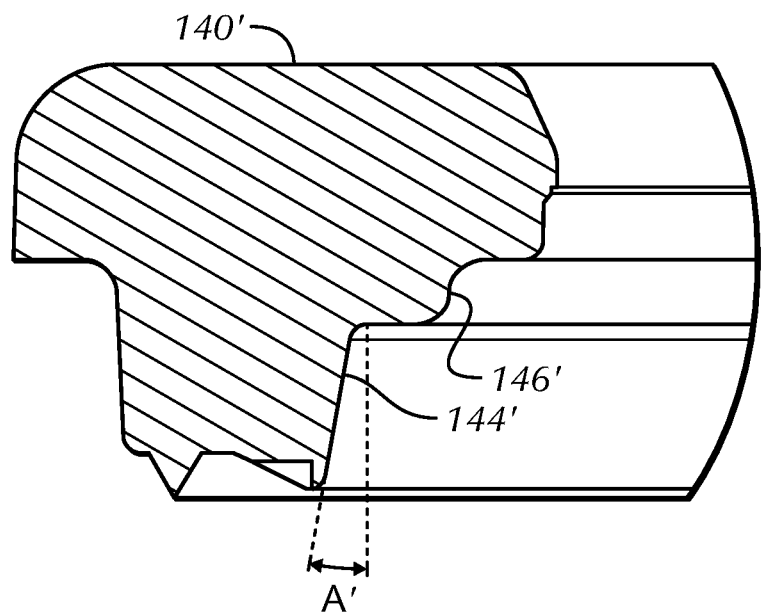
FIG. 6E is an enlarged view of a portion 6E of the cap of FIG. 6D.
Figure 6F:
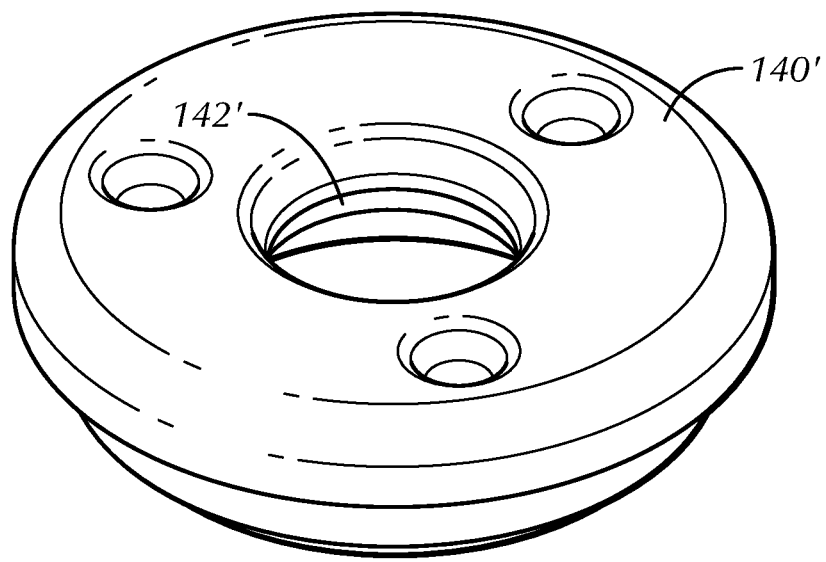
FIG. 6F is a perspective view of a cap of a medical device in accordance with at least one example of the invention.

Referring now to FIGS. 5A-6F, the medical device 100' includes the angled sidewall 144' configured to accept and retain the valve 130, 130' within the angled sidewall 144'. In some examples, the angled sidewall 144' can include discrete segments formed around the area within which the valve 130, 130' is to be positioned. In other examples, the angled sidewall 144' forms a tapered ring sized to accept the valve 130, 130' within the tapered ring. In some examples, the cap 140' includes the angled sidewall 144'. In some examples, the angled sidewall 144' is integrally formed as part of the cap 140'. In other examples, the hub housing can include the angled sidewall.

In some examples, the angled sidewall 144' is configured to compress the valve 130, 130' in order to retain the valve 130, 130' within the angled sidewall 144', effectively pinching the valve 130, 130' within the angled sidewall 144'. In some examples, the tapered ring formed by the angled sidewall 144' includes a first diameter 144A' at a proximal side of the tapered ring and a second diameter 144B' at a distal side of the tapered ring. In some examples, the first diameter 144A' is smaller than the second diameter 144B'. In other examples, the first diameter 144A' is substantially equal to the second diameter 144B'. In some examples, the angled sidewall 144' provides radial compression on the valve 130, 130'. Such radial compression improves the response of the valve 130, 130' to close upon removal of an insertable device from the valve 130, 130'.

In some examples, the angled sidewall is at an angle A' from vertical in the range of 0 degrees to 45 degrees. In some examples, the angle A' of the angled sidewall 144' is angled at about 10 degrees from vertical. With the valve 130, 130' disposed within the angled sidewall 144', in some examples, the angled sidewall 144' causes the valve 130, 130' to deform into a substantially concave shape when viewed from a proximal side (see FIG. 5D). That is, a center of the valve 130, 130' extends more distally than an outside edge of the valve 130, 130'. In other examples, the angled sidewall 144' can be configured to cause the valve 130, 130' to deform the valve 130, 130' into a substantially convex shape when viewed from the proximal side. For instance, in order to achieve a substantially convex shape of the valve 130, 130' when viewed from a proximal side, the angled sidewall 144' can be configured such that the first diameter 144A' is larger than the second diameter 144B'. In still further examples, the angled sidewall 144' can be configured to cause the valve 130, 130' to remain substantially flat rather than forming a concave shape or a convex shape when viewed from the proximal side. For instance, in order to achieve a substantially flat shape of the valve 130, 130', the angled sidewall 144' can be configured such that the angle A' from vertical is substantially 0 degrees.

In some examples, with the angled sidewall 144' included with the cap 140', the valve 130, 130' can be placed and retained within the cap 144' prior to attaching the cap 140' to the hub housing 120. In some examples, the angled sidewall can be included with the hub housing 120, in which case, the valve 130, 130' can be inserted within the angled sidewall of the hub housing 120 prior to attachment of the cap 140' to the hub housing 120.

Figure 7A:
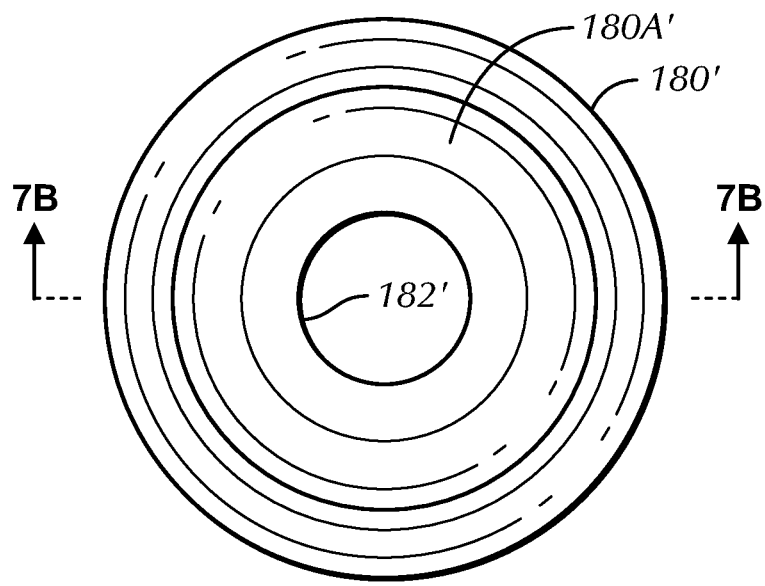
FIG. 7A is a top view of a pressure ring of a medical device in accordance with at least one example of the invention.
Figure 7B:
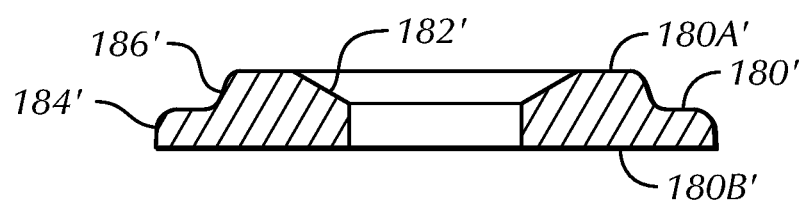
FIG. 7B is a cross-sectional view of the pressure ring of FIG. 7A taken along line 7B-7B.
Figure 7C:
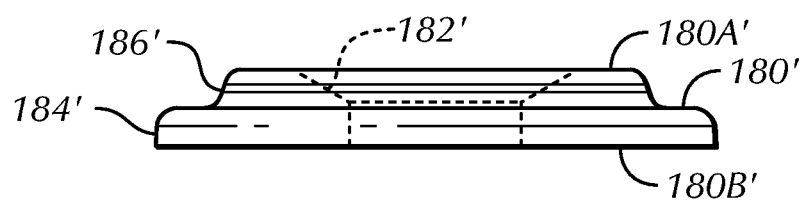
FIG. 7C is a side view of a pressure ring of a medical device in accordance with at least one example of the invention.
Figure 7D:
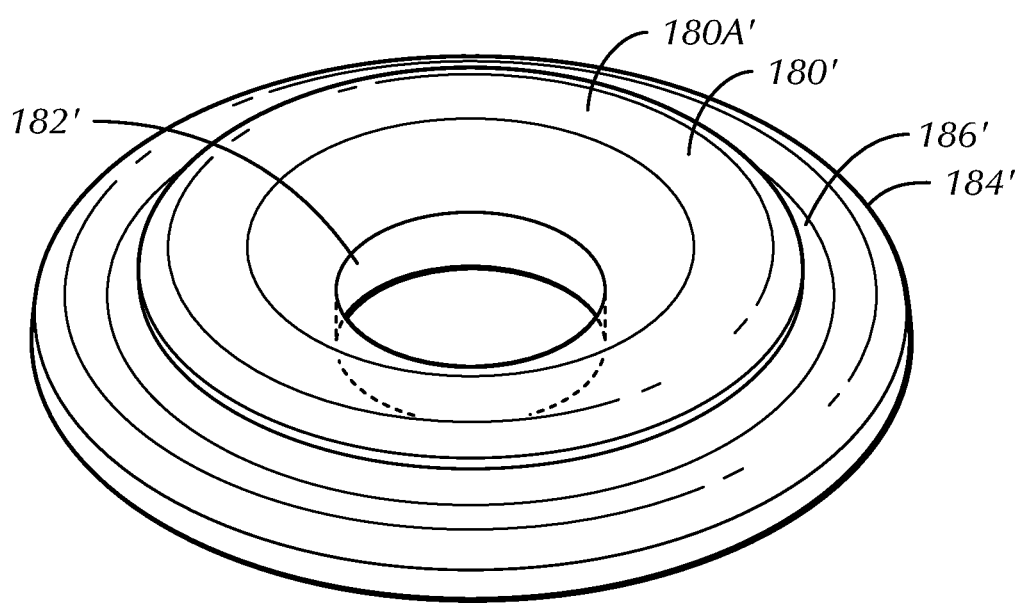
FIG. 7D is a perspective view of a pressure ring of a medical device in accordance with at least one example of the invention.

Referring now to FIGS. 5A-7D, in some examples, the medical device 100' includes a pressure ring 180' disposed between the cap 140' and the valve 130, 130', the pressure ring 180' including a proximal side 180A' and a distal side 180B'. In some examples, the pressure ring 180' includes a pressure ring opening 182' that is smaller than the opening 142' of the cap 140'. In some examples, the pressure ring 180' is disposed within the medical device 100' distally with respect to the cap 140'. In some examples, the pressure ring 180' abuts a distal side of the cap 140'. In some examples, the pressure ring 180' is complementarily shaped to fit within the cap 140'. In further examples, the pressure ring 180' includes an outer edge 184' sized and shaped to fit within the angled sidewall 144' of the cap 140'. In still further examples, the pressure ring 180' includes a shoulder 186' sized and shaped to fit within a cutout 146' of the cap 140'. In this way, the pressure ring 180' is sized and shaped to fit with the cap 140' and provide an increased surface area to abut the valve 130, 130' within the hub 110' of the medical device 100'. In some examples, the distal side 180B' of the pressure ring 180' is shaped to abut the first proximal side 130A, 130A' of the valve 130, 130' (FIG. 5D).

In some examples, with the cap 140' attached to the hub housing 120, the valve 130, 130' is compressed between the cap 140', the pressure ring 180', and the hub housing 120 to aid in retaining the valve 130, 130' in place within the medical device 100'. For instance, retention of the valve 130, 130' within the angled sidewall 144' and/or compression of the valve 130, 130' between the pressure ring 180' and the hub housing 120 can aid in retaining the valve 130, 130' in place within the medical device 100' while the insertable device is passed through the valve 130, 130'; while the insertable device is manipulated, positioned, or otherwise used within the patient; and/or while the insertable device is removed from the patient, the valve 130, 130', and/or the medical device 100'. In some examples, insertion of the insertable device through the valve 130, 130' can cause a distally-directed force on the valve 130, 130', which, in turn, can tend to pull the outer edge of the valve 130, 130' toward the center of the valve 130, 130'. By compressing the valve 130, 130' between the pressure ring 180' and the hub housing 120, in some examples, the outer edge of the valve 130, 130' can be inhibited from pulling away from the angled sidewall 144' and toward the center of the valve 130, 130', thereby maintaining the valve 130, 130' in place within the medical device 100'.

Although the examples shown and described herein are directed to a particular configuration of the pressure ring 180' and the cap 140', it should be understood that other configurations of the pressure ring and/or cap are contemplated herein. For instance, in some examples, the pressure ring and the cap can be integrally formed together. In other examples, the pressure ring can include a different shape than is shown and described herein, provided the pressure ring is able to fit between the cap and the valve 130, 130'. For instance, in some examples, the pressure ring can be configured to fit with the cap 140 of the medical device 100 of FIGS. 1A-2F. As such, the pressure ring 180' and the cap 140' shown and described herein, and, particularly the interaction between the cap 140' and the pressure ring 180', are not intended to be limiting.

In some examples, the hub housing 120 includes the tooth 128 or other projection extending from a surface of the hub housing 120 and configured to bear into the valve 130, 130' with compression of the valve 130, 130' between the cap 140' and the hub housing 120. In this way, a stress concentration is created in the valve 130, 130' to aid in retaining the valve 130, 130' in position within the medical device 100'. In some examples, the tooth 128 is annularly-shaped, extending around the entire passage 122 of the hub housing 120. In other examples, the tooth 128 can be made up of two or more discrete segments extending around the passage 122 of the hub housing 120. Although the tooth 128 is shown as being substantially triangular in shape in cross section, in other examples, other cross-sectional shapes of the tooth 128 are contemplated, including, but not limited to, rectangular, rounded, saw-tooth-patterned, or the like. Although the tooth 128 is shown extending from the hub housing 120, in other examples, it is contemplated that the tooth extends from the cap 140'. Such a configuration, in some examples, can be particularly well-suited for use with the valve deformed into the substantially convex shape when viewed from the proximal side. In further examples, each of the hub housing 120 and the cap 140' can include a tooth or other protrusion to increase compression of the valve 130, 130' between the cap 140' and the hub housing 120 and aid in maintaining the valve 130, 130' in position within the medical device 100'.

In some examples, the cap 140' is attached to the hub housing 120. In some examples, the cap 140' is attached to the hub housing 120 in a manner to inhibit the removal of the cap 140' from the hub housing, thereby helping to maintain the integrity of the medical device 100' and the fitness of the medical device 100' for use, for instance, in a procedure. In some examples, the cap 140' can be welded to the hub housing 120. In further examples, the cap 140' can be sonically welded to the hub housing 120. In various other examples, the cap 140' can be attached to the hub housing 120 in various other ways, including, but not limited to, the cap 140' being frictionally engaged, snap fit, adhesively attached, and/or attached using one or more fasteners to the hub housing 120.

In some examples, the medical device 100' provides a complete seal around the valve 130, 130'. That is, in some examples, the cap 140' is attached to the hub housing 120 (in some examples, by sonic welding, although other methods of attachment are contemplated herein) with the valve 130, 130' compressed within the angled sidewall 144', thereby axially compressing the valve 130, 130' between the pressure ring 180' and the hub housing 120. The tooth 128, in some examples, provides a concentrated axial force against the bottom of the valve 130, 130'. In this way, the radial compression of the valve 130, 130' provided by the angled sidewall 144', the axial compression of the valve 130, 130' between the pressure ring 180' and the hub housing 120 caused by the attachment of the cap 140' to the hub housing 120, and/or the concentrated axial force on the bottom of the valve 130, 130' provided by the tooth 128 contribute to providing a hemostatic seal for the medical device 100'. In some examples, the use of the pressure ring 180' within the medical device 100' allows for the medical device 100' to be used in situations with a greater pressure differential (between the patient and the ambient pressure) with little or no leakage from the valve 130, 130'. That is, in some examples, the medical device 100' can be used with little to no leakage in a situation that may cause some leakage in another similar device which does not include a pressure ring. As such, in some examples, the expected pressure differential in a procedure can lead a physician or other user to choose to use the medical device 100 over the medical device 100' (for instance, in a lower range of pressure differentials) or vice versa (for instance, in a higher range of pressure differentials). In some examples, the medical device 100, 100' can be used for a pressure differential in the range of about 0 to 5 PSI. Such a range allows the medical device 100, 100' to be used, for instance, for a radial artery of a hypertensive patient, which can have a pressure around 4 PSI. In some examples, the medical device 100, 100' can be used for a pressure differential in the range of about 0 to at least 20 PSI. In some examples, the medical device 100' can be used for a pressure differential above 20 PSI. In some examples, the medical device 100' can be used for a pressure differential up to at least 80 PSI.

In this way, in some examples, the medical device 100, 100' can be used, for instance, to gain access to a patient's vasculature for insertion of an insertable device therein. For instance, in some examples, the medical device 100, 100' can be at least partially inserted within the patient. In further examples, the sheath 160 of the medical device 100, 100' can be at least partially inserted within the patient with the hub 110, 110' remaining outside the patient. In some examples, an insertable device (such as, but not limited to a dilator, a guidewire, a catheter, or the like) can then be passed through the opening 142, 142' of the cap 140, 140'; the opening 182' of the pressure ring 180' (for the medical device 100'); the valve 130, 130'; the passage 122 of the hub housing 120; and the lumen 162 of the sheath 160 to enter the patient. From there, the insertable device can be navigated to the desired location within the patient for the particular procedure being performed. In a situation where the pressure within the patient is different than the ambient pressure outside the patient (for instance, when accessing an artery of the patient where the blood pressure is higher than the ambient pressure), in some examples, the valve 130, 130' disposed and captured within the angled sidewall 144, 144' of the medical device 100, 100' allows for the insertable device to be passed through the medical device 100, 100' while inhibiting, if not eliminating, spraying and/or leaking from the medical device 100, 100'.

In some examples, this limitation of spraying and/or leaking results from the configuration of the valve 130, 130' within the medical device 100, 100', including the manner in which the valve 130, 130' is retained within the angled sidewall 144, 144' of the medical device 100, 100'. With placement of the valve 130, 130' within the angled sidewall 144, 144', in some examples, the angled sidewall 144, 144' provides a radial compression force on the slits 132A, 132B, 132C, 132A', 132B' of the valve 130, 130'. Such a configuration, in some examples, allows for more responsive sealing of the valve 130, 130'. For instance, in some examples, the radial compression force created in the valve 130, 130' by the angled sidewall 144, 144' creates a better (for instance, quicker) response for the slits 132A, 132B, 132C, 132A', 132B' to close upon removal, insertion, or other movement of an insertable device with respect to the valve 130, 130'. The radial compression force, in some examples, allows the slits 132A, 132B, 132C, 132A', 132B' to respond quicker to minimize leaking from the slits 132A, 132B, 132C, 132A', 132B' of the valve 130, 130'.

In some examples, the angled sidewall 144, 144' can cause the valve 130, 130' to physically bow downward (that is, the valve 130, 130' is concave when viewed from the proximal side of the valve 130, 130' within the medical device 100, 100'), which can assist with the physician or other user in finding the center of the slits 132A, 132B, 132C, 132A', 132B' with insertion of the insertable device (such as, but not limited to, a dilator, a catheter, a guidewire, or other instrument) through the valve 130, 130'. In some examples, such a configuration allows for the valve 130, 130' to be formed or otherwise manufactured in a flat configuration and then bowed with insertion of the valve 130, 130' within the angled sidewalls 144, 144' of the medical device 100, 100'. In some examples, manufacturing the valve 130, 130' in a flat orientation can simplify the manufacturing process, for instance, by eliminating the step in the process of forming the valve 130, 130' into a bowed shape.

In some examples, the configuration of the angled sidewall 144, 144' for retention of and/or radial compression on the valve 130, 130' allows for the valve 130, 130' to be thinner than would otherwise be required (within a medical device having a different valve configuration, for instance), which results in reduced insertion force for inserting the insertable device through the valve 130, 130'. In some examples, the angled sidewall 144, 144' allows for a surface that will always be in contact with the side of the valve 130, 130' to better account for part tolerances. In this way, there is less impact on the performance of the valve 130, 130' and/or the medical device 100, 100' with lot-to-lot variation of the valve 130, 130' and/or mechanical properties of the material(s) of the valve 130, 130'.

In some examples, the medical device 100 can be used for insertions into an artery of the patient to allow for passage of an insertable device or other therapeutic devices through the medical device 100, 100' and into the artery. In some examples, the medical device 100, 100' can be used for insertions into a radial artery of the patient. In some examples, the sheath 160 is at least partially inserted into the patient with the hub 110, 110' remaining outside of the patient. In some examples, the EFEP material of the sheath 160 gives structural rigidity with a low profile to allow access to a location within the patient.

In some examples, the medical device 100, 100' can be inserted into a vessel of the patient, which is at a higher pressure than the ambient pressure outside of the patient. The valve 130, 130' disposed within the angled sidewall 144, 100' of the medical device 100, in some examples, allows for a hemostatic seal for the medical device 100, inhibiting, if not preventing, blood loss due to blood exiting the patient through the medical device 100, 100'. The slits 132A, 132B, 132C, 132A', 132B' in the valve 130, 130', in some examples, allow for various insertable devices (such as, for instance, a dilator, a catheter, a guidewire, or other instrument) to be passed from outside the patient to inside the patient. In some examples, the configuration of the medical device 100, 100' allows for better sealing around small-diameter insertable devices, such as, but not limited to, a dilator, a catheter, a guidewire, or the like. In some examples, the configuration of the medical device 100, 100' allows for better long-term performance, including better sealing/closing of the valve 130, 130' after removal of an insertable device from the valve 130, 130' of the medical device 100, 100'.

The present inventors have recognized various advantages of the subject matter described herein. The present inventors have recognized, among other things, that the present subject matter can be used to inhibit leakage from a medical device, such as, for instance, a catheter, a sheath, an introducer, or other access device. In various examples, the present subject matter is advantageous in that it provides increased responsiveness in sealing a hemostatic valve, thereby inhibiting spraying and excessive leaking from the valve. The present inventors have recognized the present subject matter can allow for a medical device including a thinner valve, thereby leading to reduced insertion force when inserting an instrument, device, or other object through the valve. Also, the present subject matter is advantageous in that it provides for improved manufacturing of a medical device including a hemostatic valve. While various advantages of the example systems are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A hub for a medical device, the hub including a longitudinal axis extending from a proximal side of the hub to a distal side of the hub, the hub comprising:
  a hub housing including a passage from a proximal end of the hub housing to a distal end of the hub housing;
  a valve disposed within the hub, the valve including a circumferential edge extending between a first proximal side of the valve and a second distal side of the valve, the valve being configured to allow passage of an insertable device through the valve while inhibiting leakage of fluid from the valve;
  a cap engaged to the hub housing, the cap including an opening therethrough sized and shaped to allow passage of the insertable device through the opening, the opening allowing access to the passage of the hub housing; and
  an angled sidewall disposed within the hub and abutting the circumferential edge of the valve to radially compress the valve, the angled sidewall being disposed at an angle other than parallel to the longitudinal axis of the hub housing, wherein radial compression of the valve by the angled sidewall acts to retain the valve within the hub and deform the valve into a curved shape.

2. The hub of claim 1, wherein the angled sidewall forms a tapered ring sized to accept the valve within the tapered ring.

3. The hub of claim 2, wherein the tapered ring includes a first diameter at a proximal side of the tapered ring and a second diameter at a distal side of the tapered ring, the first diameter being smaller than the second diameter.

4. The hub of claim 1, wherein the angled sidewall is configured to deform the valve into a substantially concave shape when viewed from a proximal side.

5. The hub of claim 1, wherein the cap includes the angled sidewall.

6. The hub of claim 1, comprising a pressure ring disposed between the cap and the valve, the pressure ring including a pressure ring opening that is smaller than the opening of the cap, wherein a distal side of the pressure ring is shaped to abut the first proximal side of the valve.

7. The hub of claim 1 in combination with a sheath extending distally from the distal end of the hub housing, the sheath including a lumen through the sheath, the lumen being fluidly coupled to the passage of the hub housing.

8. The hub of claim 7, wherein the sheath is at least partially formed from EFEP.

9. The hub of claim 7, wherein the sheath is overmolded with the hub housing.

10. A medical device comprising:
a hub including a longitudinal axis extending from a proximal side of the hub to a distal side of the hub, the hub including:
   a hub housing including a passage from a proximal end of the hub housing to a distal end of the hub housing;
   a valve disposed within the hub, the valve including a circumferential edge extending between a first proximal side of the valve and a second distal side of the valve, the valve being configured to allow passage of an insertable device through the valve while inhibiting leakage of fluid from the valve;
   a cap engaged to the hub housing, the cap including an opening therethrough sized and shaped to allow passage of the insertable device through the opening, the opening allowing access to the passage of the hub housing; and
   an angled sidewall disposed within the hub and abutting the circumferential edge of the valve to radially compress the valve, the angled sidewall being disposed at an angle other than parallel to the longitudinal axis of the hub housing, wherein the radial compression of the valve by the angled sidewall acts to retain the valve within the hub and deform the valve into a curved shape; and
a sheath extending distally from the distal end of the hub housing, the sheath including a lumen through the sheath, the lumen being fluidly coupled to the passage of the hub housing.

11. The medical device of claim 10, wherein the angled sidewall forms a tapered ring sized to accept the valve within the tapered ring.

12. The medical device of claim 11, wherein the tapered ring includes a first diameter at a proximal side of the tapered ring and a second diameter at a distal side of the tapered ring, the first diameter being smaller than the second diameter.

13. The medical device of claim 10, wherein the angled sidewall is configured to deform the valve into a substantially concave shape when viewed from a proximal side.

14. The medical device of claim 10, wherein the cap includes the angled sidewall.

15. The medical device of claim 10, wherein the valve includes at least one slit within the valve, the slit extending from the first proximal side of the valve to the second distal side of the valve, the slit being angularly rotated within the valve from the first proximal side to the second distal side.

16. The medical device of claim 15, wherein the at least one slit includes at least two intersecting slits within the valve.

17. The medical device of claim 10, wherein the valve includes:
a first slit extending partially through the valve from the first proximal side of the valve; and
a second slit extending partially through the valve from the second distal side of the valve, the second slit being angularly offset from the first slit, the first and second slits intersecting at a location within the valve intermediate the first proximal side and the second distal side.

18. The medical device of claim 10, comprising a pressure ring disposed between the cap and the valve, the pressure ring including a pressure ring opening that is smaller than the opening of the cap, wherein a distal side of the pressure ring is shaped to abut a first proximal side of the valve.

19. The medical device of claim 10, wherein the sheath is at least partially formed from EFEP.

20. The medical device of claim 10, wherein the sheath is overmolded with the hub housing.

* * * * *